Figure 2:
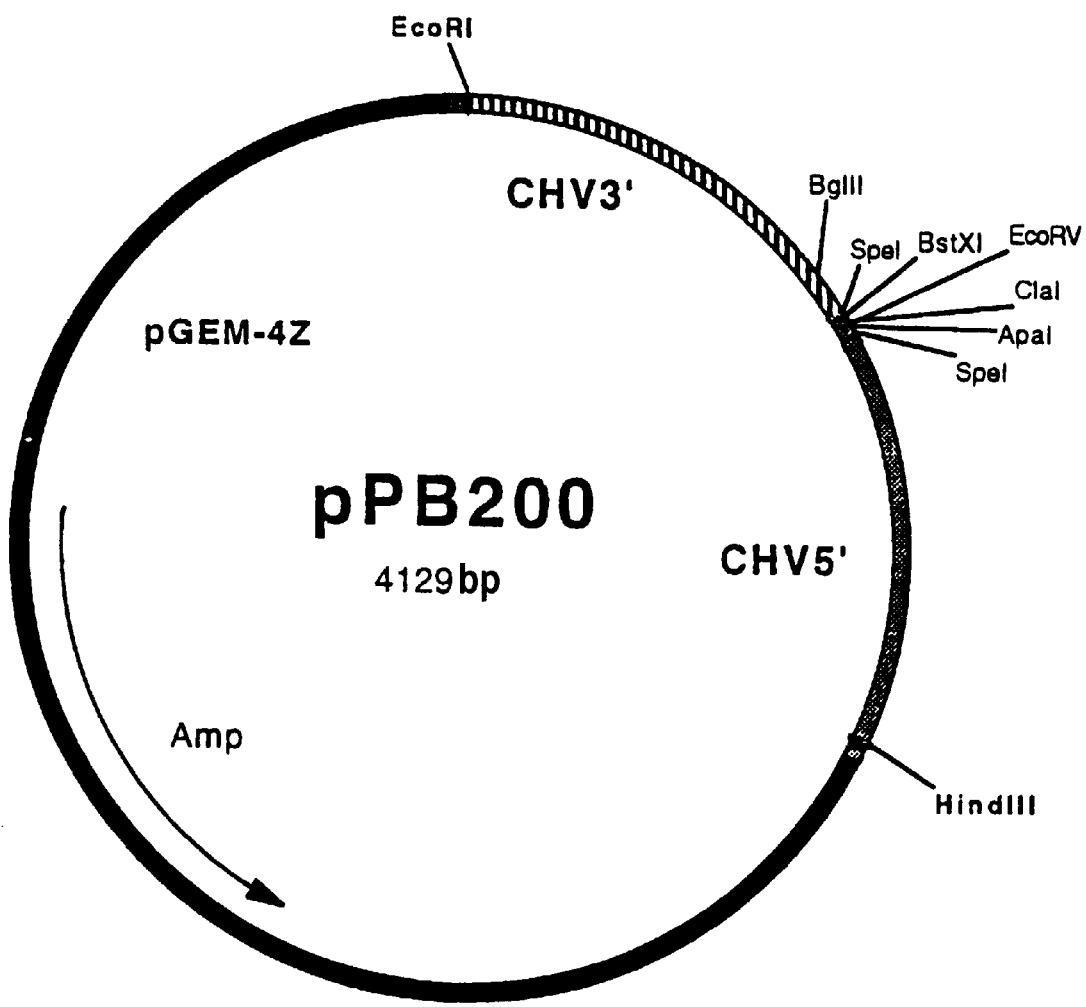

United States Patent [19]

Audonnet et al.

[11] Patent Number: 6,159,477
[45] Date of Patent: Dec. 12, 2000

[54] CANINE HERPESVIRUS BASED RECOMBINANT LIVE VACCINE, IN PARTICULAR AGAINST CANINE DISTEMPER, RABIES OR THE PARAINFLUENZA 2 VIRUS

[75] Inventors: Jean-Christophe Audonnet, Lyons; Philippe Baudu, Craponne, both of France

[73] Assignee: Merial, Lyons, France

[21] Appl. No.: 09/213,053

[22] Filed: Dec. 16, 1998

Related U.S. Application Data

[63] Continuation of application No. PCT/FR97/01115, Jun. 23, 1997.

[30] Foreign Application Priority Data

Jun. 27, 1996 [FR] France ..................................... 9608242

[51] Int. Cl.[7] .......................... A61K 39/12; A61K 39/27; A61K 39/175; C12N 15/00
[52] U.S. Cl. ..................................... 424/199.1; 424/229.1; 424/704.1; 424/213.1; 435/320.1; 536/23.72
[58] Field of Search ............................. 424/229.1, 199.1, 424/204.1, 818, 213.1; 935/65; 536/23.72; 435/320.1

[56] References Cited

U.S. PATENT DOCUMENTS

| | | |
|---|---|---|
| 4,213,965 | 7/1980 | Carmichael . |
| 5,356,622 | 10/1994 | Heath et al. . |
| 5,399,485 | 3/1995 | Regnery et al. . |
| 5,418,137 | 5/1995 | Yamanaka et al. . |
| 5,681,724 | 10/1997 | Tripp et al. . |
| 5,707,817 | 1/1998 | Wisnewski et al. . |
| 5,753,235 | 5/1998 | Haanes et al. ........................ 424/229.1 |
| 5,789,194 | 8/1998 | Tripp et al. . |
| 5,795,768 | 8/1998 | Tripp et al. . |
| 5,804,197 | 9/1998 | Haanes et al. ........................ 424/229.1 |

FOREIGN PATENT DOCUMENTS

| | | |
|---|---|---|
| WO 92 13560 | 8/1992 | WIPO . |
| WO 93/10225 | 5/1993 | WIPO . |
| WO 93/23077 | 11/1993 | WIPO . |
| WO 94/15593 | 7/1994 | WIPO . |
| WO 94/17813 | 8/1994 | WIPO . |
| WO 94/17824 | 8/1994 | WIPO . |
| WO 95/24198 | 9/1995 | WIPO . |
| WO 95/32988 | 12/1995 | WIPO . |
| WO 96/11271 | 4/1996 | WIPO . |
| WO 96/11706 | 4/1996 | WIPO . |

OTHER PUBLICATIONS

U.S. Ser. No. 08/401,509 (no patent publication).
U.S. Ser. No. 08/473,034 (no patent publication).
U.S. Ser. No. 08/482,304 (no patent publication).
U.S. Ser. No. 08/485,434 (no patent publication).
K.J.. Limbach, et al, "Nucleotide sequence of the genes encoding the canine herpesvirus gB, gC and gD homologues", Journal of General Virology, vol. 75, (Aug. 1994) pp. 2029–2039.
M. Redmond, et al, "Gene organization in the UL region and inverted repeats of the canine Herpesvirus genome", Journal of General Virology, (Jan. 1996) 77 (PT 1), pp. 37–48.
M. Redmond, "Sequence of the canine herpesvirus thymidine kinase gene: taxon–preferred amino acid residues in the alphaherpesviral thymidine kinases", Viirus Res. (1995), 39(2–3), pp. 341–354.

*Primary Examiner*—Ali Salimi
*Attorney, Agent, or Firm*—Frommer Lawrence & Haug LLP; William S. Frommer; Thomas J. Kowalski

[57] ABSTRACT

Disclosed and claimed is a recombinant canine herepes virus (CHV). The recombinant CHV includes and expresses at least one heterologous nucleotide sequence encoding an antigen. The antigen can be canine distemper virus HA, canine distemper virus F, rabies virus G, canine parvovirus VP2, parainfluenza virus type 2 HA, parainfluenza virus type 2 F, *Borrelia burgdorferi* OspA, or *Borrelia burgdorferi* OspB. The at least one heterologous nucleotide sequence can be in at least one insertion site selected from the group consisting of ORF3 (SEQ ID NO:4), ORF5 (SEQ ID NO:5), the thymidine kinase gene, and the intergenic region corresponding to genes coding for the large subunit and the small subunit. Immunological or vaccine compositions as well as methods for inducing an immunological response are also disclosed and claimed.

31 Claims, 18 Drawing Sheets

```
        XhoI
    1   CTCGAGGAAATTGTTTGTTTGTATCTACAAAACTTCAAAATATCTTTGTTTATTGTCTCTTCGATGGATT
   71   TTATTTTCATCTTCGCGATTGATTCTTCCTTGGTTACCGTAATTTATAAATAAACACAATAAAAATTAAG
  141   TTTAAAAACAATTTTATTAAACCCATCGTCTTGATTTACTATCATCCCAGTAGGAAATTAGAACTAGATT
                    399◄•••ValTrpArgArgSerLysSerAspAspTrpTyrSerIleLeuValLeuAsn
  211   ATAATCTATCGGTATAGAAATATGTTTCCAAAATAAATTAGTTAAATTTTTAGCCTTTTCTTTATCATCT
  381◄TyrAspIleProIleSerIleHisLysTrpPheLeuAsnThrLeuAsnLysAlaLysGluLysAspI
        HindIII
  281   ATAAAGCTTAAAAGTGTTTCATAAACAAGATTTATATCAAACTTTTCTTGGATAATTGGAACTCTTTTAA
  357◄lePheSerLeuLeuThrGluTyrValLeuAsnIleAspPheLysGluGlnIleIleProValArgLysIl
  351   TTATAGATAAATTTTCACCCCTATATTCTGGGGTTATCATATTTGTTAGATGTTTAATAAATTTTCTCTC
  334◄eIleSerLeuAsnGluGlyArgTyrGluProThrIleMetAsnThrLeuHisLysIlePheLysArgGlu
  421   CAACACTTCGTGTTTGGTTTGGGGTGCCGGAAGCATCATTAAAGAACGGGATATCGTTTTCATTATTGGT
  311◄LeuValGluHisLysThrGlnProAlaProLeuMetMetLeuSerArgSerIleThrLysMetIleProP
  491   GGAAATCTTGATGTATATTTTAAATTTAAACTATTCTCATCAACAGCTGTTACGCGCTTTGATTGTCCTT
  287◄roPheArgSerThrTyrLysLeuAsnLeuSerAsnGluAspValAlaThrValArgLysSerGlnGlyLy
  561   TATTTGATGGAGAGTTTATTTTTGATAAAATTTTAAATCCATTTTGATTTTTTGGTATACCAAATGAATC
  264◄sAsnSerProSerAsnIleLysSerLeuIleLysPheGlyAsnGlnAsnLysProIleGlyPheSerAsp
  631   GGTATCACTACTTTCACTACTGGTAATATTTGAGGATTCTTCGGATGATGAAACTATATTTGTAGAAACA
  241◄ThrAspSerSerGluSerSerThrIleAsnSerSerGluGluSerSerSerValIleAsnThrSerValS
  701   GAATCACTTATTCTCCATGAGTTTGATATTTGATCTAAATATTTTTCATGATGTTGTATTTCTCCTGATT
  217◄erAspSerIleArgTrpSerAsnSerIleGlnAspLeuTyrLysGluHisHisGlnIleGluGlySerGl
  771   CTTCAGATGAATCTCCACTATCAGAATTATATTCCTTTTTACTATTTTTATATTTATTTTTAATAATTGA
  194◄uGluSerSerAspGlySerAspSerAsnTyrGluLysLysSerAsnLysTyrLysAsnLysIleIleSer
  841   TTGAACAGATTTTAAAATAGGGGCTTGGTGCAAGTCTGTATGACAGCGAACAAACGTACATAAAAACTCA
  171◄GlnValSerLysLeuIleProAlaGlnHisLeuAspThrHisCysArgValPheThrCysLeuPheGluP
  911   GGATATGATACATTTAAAGAAGCAAGTATATCCCTACATCGGAGGGTGGGTGGAAAAAGAGGTACAACAT
  147◄roTyrSerValAsnLeuSerAlaLeuIleAspArgCysArgLeuThrProProPheLeuProValValAs
  981   CCAATATAATATCACAACCCATTAATATTAGATCAGTATCCGTTGTATATATTTGAGCGGCTGTATTAGT
  124◄pLeuIleIleAspCysGlyMetLeuIleLeuAspThrAspThrThrTyrIleGlnAlaAlaThrAsnThr
 1051   ATGATAAAGATTAGCACAAACATCATCAGCTTCCATATCAGATACATTAACATATGGAAAACCCAAATGG
  101◄HisTyrLeuAsnAlaCysValAspAspAlaGluMetAspSerValAsnValTyrProPheGlyLeuHisA
 1121   CGTATTAAATTAACACATAATTTATAACATAACTTAGGAGTATTTACAAGTGAGCTCCATCGTGCTGATA
   77◄rgIleLeuAsnValCysLeuLysTyrCysLeuLysProThrAsnValLeuSerSerTrpArgAlaSerLe
 1191   AAATATTTATAGGTTCACATTTTTCCAATTTTTTGTAAGTTTTTAAAATTTCCCCACATACATTATCCTT
   54◄uIleAsnIleProGluCysLysGluLeuLysLysTyrThrLysLeuIleGluGlyCysValAsnAspLys
 1261   AATGGAATTTCTCCAAGTCTTCCAGATCCTCCTTGATGACACATAGTTTGTGTGGCGATACGTTTGCTCC
   31◄IleSerAsnArgTrpThrLysTrpIleArgArgSerSerValTyrAsnThrHisArgTyrThrGlnGluV
                    ◄---ORF1                                    BglII
 1331   ACGTTTAACATGTCCATCACCATTTATACCACGATCTGAAACAAAAATTGGAAAATAAGATCTTTTTTGG
    7◄alAsnLeuMetAspMetValMet
 1401   AGTAATTTAAGTAAAGAAAAAAAACATTCAGCTGTTACAGTGGGACTATCCGTTTGAGTATCATTTTCTA
 1471   TACAAAATTTTTCCATCAACGTATACATTACATTCCATAAGTCAATTGCGATTGGTGTACAATACCAGGT
                                                            SpeI
 1541   GGTGTTGCTATCGCATCGTGTTTAACTAGTCTACGACTATAAGCATATTTCAAAAGTCCAAAAAGACCCA
                                                                SpeI
 1611   TTTTAATAAAATACCAAACAGAACCTTTTCGACAAACTAAATGAATAAAACTAGTTTTTAAGTATTAAAT
```

FIGURE 1A

FIGURE 1

| 1A | 1B | 1C | 1D |

ORF2--->
```
1681 ATAACCTTTAACTAAATTAATTAAATAATGATTAATTTAAAAACCGAAATACAAATATTTTTTAGTCAAG
                       1▶MetIleAsnLeuLysThrGluIleGlnIlePhePheSerGlnA
1751 ATTTTATGAAATCAATCAAAATCACCACAATTATGCAAATGAACCCACCTACCAACGTCATCAAAACTAA
       15▶spPheMetLysSerIleLysIleThrThrIleMetGlnMetAsnProProThrAsnValIleLysThrAs
1821 TTTAGTCTATAAAAAGAAATTGTTAACATTTAGTTTAAATTTAAACTTTTATTTCTTAAAATTTTTATTA
       38▶nLeuValTyrLysLysLysLeuLeuThrPheSerLeuAsnLeuAsnPheTyrPheLeuLysPheLeuLeu
1891 TTTTGCTTAGTTTTTAAGGCGATGGCGTGTTTTCGTCCTAAAACTGAATTTAAGATAACCAACCATCCAT
       62▶PheCysLeuValPheLysAlaMetAlaCysPheArgProLysThrGluPheLysIleThrAsnHisProS
1961 CTCAGATTATAAATAACGAAGAAAATATAAACTCTGAAGAAGGAAAATTTATATCTGGTCGTGCTGTTTT
       85▶erGlnIleIleAsnAsnGluGluAsnIleAsnSerGluGluGlyLysPheIleSerGlyArgAlaValLe
         HindIII
2031 GGAAGATCAAAAGCTTCGTGATGTGATAAGTATGCTAACACCCTTTTCAACTAGCTTGAAAAACTCTTTT
       108▶uGluAspGlnLysLeuArgAspValIleSerMetLeuThrProPheSerThrSerLeuLysAsnSerPhe
                                                       SpeI
2101 ATAGTTTTTAGTGACTATGGGATGATGATCCATACTAGTATTTGTGGAGAACAAATTTACATTCCTATTT
       132▶IleValPheSerAspTyrGlyMetMetIleHisThrSerIleCysGlyGluGlnIleTyrIleProIleS
2171 CTAAAAACCAATTTTCTTCTTATTTTTGGGGATATAGCGACCCTGCGGTATTTTTGGCAAATGTTGATAG
       155▶erLysAsnGlnPheSerSerTyrPheTrpGlyTyrSerAspProAlaValPheLeuAlaAsnValAspSe
2241 TAAAAGGGGATTGTTGGATGTTTTTAAATCAACAAGTAAAATGTCTAAAGTATTCTTTGAAATAAGTAAC
       178▶rLysArgGlyLeuLeuAspValPheLysSerThrSerLysMetSerLysValPhePheGluIleSerAsn
2311 CCTTCCCAACATAGAATGTTAAAACAAGTTATTTTTACTATAAGTGATAGTAATATAAAATGCTCTACAC
       202▶ProSerGlnHisArgMetLeuLysGlnValIlePheThrIleSerAspSerAsnIleLysCysSerThrL
2381 TTCTAAAAGCTGAATTTAGTAACTATTGTATTATGCTTCCATCAAGAAATCCGGACTTTAGTCTTGAACT
       225▶euLeuLysAlaGluPheSerAsnTyrCysIleMetLeuProSerArgAsnProAspPheSerLeuGluLe
2451 TAATAAATATCAATTAAATAAAATACTCGAACTAAACAAAAAACAAAATTCATTGTTAAAATTTGAATCT
       248▶uAsnLysTyrGlnLeuAsnLysIleLeuGluLeuAsnLysLysGlnAsnSerLeuLeuLysPheGluSer
2521 AATGAAAATAATGTTGTGATTTCATCTGAAAGTGGAAGTGTTTCATTGAATTTGGATAGAAGCGATTCTG
       272▶AsnGluAsnAsnValValIleSerSerGluSerGlySerValSerLeuAsnLeuAspArgSerAspSerG
2591 AAGGAGAAGATAGCGCATCGATTTTAAAATCTGCTACAAAAAAAGTAAATCCTTATCTAGTTAAACACTC
       295▶luGlyGluAspSerAlaSerIleLeuLysSerAlaThrLysLysValAsnProTyrLeuValLysHisSe
2661 AGAAAATTTCAAACGTTTAAAATTTCGTTGGATGATTATACCAATTTTTTTCCTCTTTTGAAAAAACTA
       318▶rGluAsnPheLysArgLeuLysPheArgTrpMetIleIleProIlePhePheProLeuLeuLysLysLeu
                                                                            HindIII
2731 AAACTAACAAATACAACAGTATCGATAAATTTCTTTTTTACTCCAACTACCAATCCCATGATAAGCTTGA
       342▶LysLeuThrAsnThrThrValSerIleAsnPhePhePheThrProThrThrAsnProMetIleSerLeuT
2801 CGTCAAGTAAACCAATTGGAATTATACTGTTTTTCTTTTGTACCAATGAATTGCAACATAAGAGCCTGAA
       365▶hrSerSerLysProIleGlyIleIleLeuPhePhePheCysThrAsnGluLeuGlnHisLysSerLeuLy
2871 GCGCCCAGCATCTCCATCAGATGAAGAAAAGCCACCAAAAATCCAATGTGGATTTTTTAGTCAACATTTT
       388▶sArgProAlaSerProSerAspGluGluLysProProLysIleGlnCysGlyPhePheSerGlnHisPhe
2941 GTAAATACGGATGTTAATATTAAACCCAATTAAATGACGTAAAATGATAAATTGTATTTAAAGAGAAGT
       412▶ValAsnThrAspValAsnIleLysPro•••
              HindIII          ORF3--->
3011 TTTTTCCAAAAGACAAGCTTTTATTAATAATGTCACTAGAAGATAATAATGTACAATCGTTTGATCAACT
                           1▶MetSerLeuGluAspAsnAsnValGlnSerPheAspGlnLe
3081 GGAACCTCCTATTACATCATTTTCTATAATAAATTGCTCTGGATCGAGACCTGGATGTCTACCATGTATG
       14▶uGluProProIleThrSerPheSerIleIleAsnCysSerGlySerArgProGlyCysLeuProCysMet
```

FIGURE 1B

FIGURE 1

| 1A | 1B | 1C | 1D |

```
3151 TATGTAACTACAAAATCACTTCTATGTATTGGACTTCAAGCTGGAATTTTAACAGCCTTAATTATATTAA
  38▶ TyrValThrThrLysSerLeuLeuCysIleGlyLeuGlnAlaGlyIleLeuThrAlaLeuIleIleLeuI
3221 TTCAAATATTAACTGAAAGTTTCGTATGTTCTATAATTCTTATAGCAACTGTGTTAATATTTACGCTATC
  61▶ leGlnIleLeuThrGluSerPheValCysSerIleIleLeuIleAlaThrValLeuIlePheThrLeuSe
3291 AAAAATATCTATTTCTACTTCTGAAAAAATTTCTTCTATTTGTAGAATTAGTCAGTCGATATTTGTAACA
  84▶ rLysIleSerIleSerThrSerGluLysIleSerSerIleCysArgIleSerGlnSerIlePheValThr
3361 ATAGCCGCCTTTTGTTGGGGGTTTGATTGGATATTAAATCCAATAGCAATTAAAATAATTCTTATATTAA
 108▶ IleAlaAlaPheCysTrpGlyPheAspTrpIleLeuAsnProIleAlaIleLysIleIleLeuIleLeuS
3431 GTTTATCATTTTTAACTATTTGTACAATAAAAATACATATATTTTATTTGATAAGTATATTAAATGGTTC
 131▶ erLeuSerPheLeuThrIleCysThrIleLysIleHisIlePheTyrLeuIleSerIleLeuAsnGlySe
3501 TGGATCTCATGTAAAAGGATCGCTAGTAACAATATTGTTTGGAACTATACTAGGTGTATTTGGAACTCTT
 154▶ rGlySerHisValLysGlySerLeuValThrIleLeuPheGlyThrIleLeuGlyValPheGlyThrLeu
3571 AATGTTATTAAAATAGAAATTTTAATTGGATTTGGTATAGCACTTTGTATAATTTTATCTAACACCAACT
 178▶ AsnValIleLysIleGluIleLeuIleGlyPheGlyIleAlaLeuCysIleIleLeuSerAsnThrAsnP
         SpeI                                                     BglII
3641 TTGGACTAGTAATTAGAGATACATGCTATTATCGTATAGGAAGATATAAATTAATGAGAACTTTTACAGA
 201▶ heGlyLeuValIleArgAspThrCysTyrTyrArgIleGlyArgTyrLysLeuMetArgThrPheThrAs
3711 TCTTGGACATGGAGCGTCTTACTCAATAGAGGAAGATGAAACCTCTGATTACAGTGAAATACATGAAAGA
 224▶ pLeuGlyHisGlyAlaSerTyrSerIleGluGluAspGluThrSerAspTyrSerGluIleHisGluArg
3781 AAAATTAGTAGTTTTCAACTAATTTATAAATATCCAAGTATGATAATAATTTCTATTTTAGGATTTATGT
 248▶ LysIleSerSerPheGlnLeuIleTyrLysTyrProSerMetIleIleIleSerIleLeuGlyPheMetL
3851 TAACTATAGCTATTTGGGGATTAAATGTATACTTAAAAAATTTAAAATTTCATTCTCCTTTTACACTTGT
 271▶ euThrIleAlaIleTrpGlyLeuAsnValTyrLeuLysAsnLeuLysPheHisSerProPheThrLeuVa
3921 TATTAGCTTTATTGTTGGTCATTGTTTAGCATTCTTAGTTGAACCGTTTAACTATAAGATTAAATGTATA
 294▶ lIleSerPheIleValGlyHisCysLeuAlaPheLeuValGluProPheAsnTyrLysIleLysCysIle
3991 TCACGAATTATACTAATTATTTGTCTTTTACTAGAATTAATTGCTTCACTTATTTCTGTACTAGGATTAA
 318▶ SerArgIleIleLeuIleIleCysLeuLeuLeuGluLeuIleAlaSerLeuIleSerValLeuGlyLeuA
4061 ATTTTGGATCACCATTAATCTTGACAACAACTACTACAATTTCGTTAGTTTCACTTTTGTATATACGAAA
 341▶ snPheGlySerProLeuIleLeuThrThrThrThrThrIleSerLeuValSerLeuLeuTyrIleArgLy
4131 ACAAACACAAGGTGTAAACCGTCTTGCTGCCACATATATTTCACGAGCCCTAATTATTGGTTTGTATATG
 364▶ sGlnThrGlnGlyValAsnArgLeuAlaAlaThrTyrIleSerArgAlaLeuIleIleGlyLeuTyrMet
4201 ACTGTTGGAATTTGTTACATTTTTATTAAAACAATAAATTAAATTTTTTAAACTATATTACGGTTGTGTG
 388▶ ThrValGlyIleCysTyrIlePheIleLysThrIleAsn•••
         EcoRI
4271 TGTTTTAAGTTTTAAATAAAGCAATATTTCGAATTCACATTTATCAAAAACATTAAAACCCAACACAAAA
         ORF4 --->
4341 AAATTTCTATAATCATTAAGGTAATAAGTCAAAATGAGTTTTAAAAATTTTTATCTAATATATGTAATTA
                                    1▶MetSerPheLysAsnPheTyrLeuIleTyrValIleI
4411 TAATTTTTATAAACTCGATAATAACTTCGGCATCTACATCCAAACCTTCAACACCTACCATAATTCCAAC
  13▶ leIlePheIleAsnSerIleIleThrSerAlaSerThrSerLysProSerThrProThrIleIleProTh
4481 TTCAGCAAATGAATCACCTGCTTCCATAGATACAACTATAACAAAACCTATATCTACAGAGGCAAATAAT
  36▶ rSerAlaAsnGluSerProAlaSerIleAspThrThrIleThrLysProIleSerThrGluAlaAsnAsn
4551 TTAAAATCAGTAAGTACCTCAATTAAACCACCTAAAAACTTAAAAAAAAAATTACTTAAATCTAAATGTA
  60▶ LeuLysSerValSerThrSerIleLysProProLysAsnLeuLysLysLysLeuLeuLysSerLysCysA
4621 GAGATAATGTTATTTATAGGCCATATTTTAGTCAATTAGAAATTAACTGTACTATAACTAAAAAGCAAAA
  83▶ rgAspAsnValIleTyrArgProTyrPheSerGlnLeuGluIleAsnCysThrIleThrLysLysGlnAs
4691 TTTAAGTAATCCTTTAATTGAGTTATGGTTTAAAGAACTTTCTACATATAATAAAACCAATGAAAATGTT
 106▶ nLeuSerAsnProLeuIleGluLeuTrpPheLysGluLeuSerThrTyrAsnLysThrAsnGluAsnVal
4761 GAAAGTTTAAAAACAGATATATCAAAAAATATTTTATTATTTTCGACAAAAAATAATAGTGATAACTTTT
 130▶ GluSerLeuLysThrAspIleSerLysAsnIleLeuLeuPheSerThrLysAsnAsnSerAspAsnPheT
```

FIGURE 1C

FIGURE 1

| 1A | 1B | 1C | 1D |

```
4831 ATAATGATTTTTTATTAGGTATACAAAATCAACCAGTAAATTATAAACTTTACGGTTCCCAATTTTATGA
 153▶yrAsnAspPheLeuLeuGlyIleGlnAsnGlnProValAsnTyrLysLeuTyrGlySerGlnPheTyrAs
4901 TAATGGAAACATATTACTAAATATAAAGTCGGTTGACTTTAAAACCTCTGGAATATATACTTGGAAACTA
 176▶pAsnGlyAsnIleLeuLeuAsnIleLysSerValAspPheLysThrSerGlyIleTyrThrTrpLysLeu
4971 TATAATTCAAATAATGAAAGTATTTTTGAAACTTTTAAAATTCAAGTATATGCATATCATTCACCAAATG
 200▶TyrAsnSerAsnAsnGluSerIlePheGluThrPheLysIleGlnValTyrAlaTyrHisSerProAsnV
5041 TAAACTTAAAATCAAACCCAAGTTTATATAATGAAAACTACAGCGCTATTTGTACAATAGCAAATTACTT
 223▶alAsnLeuLysSerAsnProSerLeuTyrAsnGluAsnTyrSerAlaIleCysThrIleAlaAsnTyrPh
5111 TCCATTGGAATCTACGGAAATATTTTGGTTTAACGATGGACAACCTATTGATAAAAAATATATAGATGAA
 246▶eProLeuGluSerThrGluIlePheTrpPheAsnAspGlyGlnProIleAspLysLysTyrIleAspGlu
5181 ACTTATAGTGTATGGATTGACGGTCTTATAACACGCACTTCAATATTATCCCTTCCCTTTTCCGAAGCCA
 270▶ThrTyrSerValTrpIleAspGlyLeuIleThrArgThrSerIleLeuSerLeuProPheSerGluAlaM
5251 TGGAAAGCCCCCCCAATTTGCGATGTAATGTTGAATGGTATAAAAATTCAAAGGCCTCAAAAAAATTTTC
 293▶etGluSerProProAsnLeuArgCysAsnValGluTrpTyrLysAsnSerLysAlaSerLysLysPheSe
5321 AAATACCGTTATTCCAAAAGTTTACTATAAACCTTTTATATCTATAAAATTTGATAATGGTTTAGCTATT
 316▶rAsnThrValIleProLysValTyrTyrLysProPheIleSerIleLysPheAspAsnGlyLeuAlaIle
5391 TGTGATGCTAAATGTGTTTCCCGTGAAAATAATAAATTACAATGGTTAGTTAAAGATATACCTATAAATG
 340▶CysAspAlaLysCysValSerArgGluAsnAsnLysLeuGlnTrpLeuValLysAspIleProIleAsnG
5461 GTGATGATATTATAAGCGGCCCCTGTTTAAACCACCCTGGTTTGGTCAATATTCAAAATAAAATAGATAT
 363▶lyAspAspIleIleSerGlyProCysLeuAsnHisProGlyLeuValAsnIleGlnAsnLysIleAspIl
5531 ATCGGATTATGATGAACCTGTTACCTATAAATGTTCAATTATTGGTTATCCAATAATTTTTCCCAACTTT
 386▶eSerAspTyrAspGluProValThrTyrLysCysSerIleIleGlyTyrProIleIlePheProAsnPhe
5601 TATGATGAAAAGGTGTTTGATGCATCGGATGAAAATGTTAGTAAATCGATGTTAATAAGTATTACCACAA
 410▶TyrAspGluLysValPheAspAlaSerAspGluAsnValSerLysSerMetLeuIleSerIleThrThrI
5671 TAATTGGTGGAGCCATTTTTGTTATAGTATTGATTTTTATAACAGCTTTATGTTTTTATTGTTCAAAAAA
 433▶leIleGlyGlyAlaIlePheValIleValLeuIlePheIleThrAlaLeuCysPheTyrCysSerLysAs
                  BglII
5741 TAATAAGATCTAATATCAATATTTACGTAAATGGATTATATAATGTTATATTCGTGTTATTATGATTTAT
 456▶nAsnLysIle•••
                                                                    ORF5--->
5811 AAGTTCATCAAATTTAAAAATTTGTATAGTATTAAGATTTTTAATAGGGGTATCGTTTAATATGGCTCAG
                                                                 1▶MetAlaGln
5881 TTAGTTTTAACTGATATTCCCCTCGAAGATGTGGAAAATAAAAATACTTCATCCGACGAAGAAACAACTA
   4▶LeuValLeuThrAspIleProLeuGluAspValGluAsnLysAsnThrSerSerAspGluGluThrThrA
5951 ACTTAAACCAGAAAAAATCAACATGTCAATGTTTATGTGTTACCCTTGGATTTTTTGCAGCTGGAATTTT
  27▶snLeuAsnGlnLysLysSerThrCysGlnCysLeuCysValThrLeuGlyPhePheAlaAlaGlyIleLe
6021 ATTAACCATAGCTGCAATAATTTTTACTTTTATTTTTACAGTACCATTAGAAATGCTTGGATCGATTAAT
  50▶uLeuThrIleAlaAlaIleIlePheThrPheIlePheThrValProLeuGluMetLeuGlySerIleAsn
6091 TGTCCTCCATCTACATTTGGTATTGATAATGTTTGTATCGAACCAATAAAAAAATCTATTAATTCTTATT
  74▶CysProProSerThrPheGlyIleAspAsnValCysIleGluProIleLysLysSerIleAsnSerTyrS
                                                                       ScaI
6161 CAGAATTATCTAAAATATGTTATGATAGATTGTCAAATCCGATAAATCAGAGTACT
  97▶erGluLeuSerLysIleCysTyrAspArgLeuSerAsnProIleAsnGlnSerThr
```

FIGURE 1D

FIGURE 1

| 1A | 1B | 1C | 1D |

FIGURE 6

CANINE HERPESVIRUS BASED RECOMBINANT LIVE VACCINE, IN PARTICULAR AGAINST CANINE DISTEMPER, RABIES OR THE PARAINFLUENZA 2 VIRUS

This is a continuation of copending International Application PCT/FR97/01115 having an international filing date of Jun. 23, 1997, designating the U.S. and claiming priority.

The present invention relates to vaccines, preferably for dogs, produced from recombinant canine herpesviruses, and to the methods for obtaining and preparing these recombinant viruses. The present invention relates more especially to recombinant canine herpesviruses comprising an expression cassette for one or more foreign gene(s).

Canine herpesvirosis is caused by the canine herpesvirus (CHV). The canine herpesvirus (CHV) is classified in the *Alphaherpesvirinae* family. This herpesvirus is a major pathogen for neonatal puppies. Canine herpesvirosis manifests itself chiefly in a haemorrhagic disease in puppies, and in a benign disease of the upper respiratory apparatus in adult dogs. There are at present no vaccines for protecting puppies against canine herpesvirosis.

Moreover, domestic dogs are exposed to numerous other diseases, and the development of a vaccinal vector capable of expressing different antigens of canine pathogenic agents would enable the efficacy of vaccination programmes to be simplified and improved, especially for puppies in breeding kennels. Among pathogenic agents of importance for dogs, the Carré's disease virus, the Rubarth's hepatitis virus, the rabies virus, the canine parvovirosis virus, the canine coronavirus, the parainfluenza virus type 2, *Bordetella bronchiseptica, Borrelia burgdorferi, Leptospira spp.* and *Leishmania infantum* may be mentioned.

Little is known about the CHV virus genome. The genomic organization of this virus was published only recently (Rémond M. et al. J. Gen. Virol. 1996. 77. 37–48), and the genes for the three major glycoproteins gB, gC and gD, as well as a gene designated CHV ORF2, have been described (K. Limbach et al. J. Gen. Virol. 1994. 75. 2029–2039).

Following their work on CHV, the inventors have succeeded in determining several regions which are nonessential for replication in vitro, which have proved useful for the construction of recombinant CHV viruses. The inventors are hence in a position to put forward for the first time the CHV virus as a vaccination vector for dogs. It was found that the vaccinal vectors according to the invention had particular advantages for the vaccination of dogs. In effect, the canine herpesvirus is very species-specific and possesses a large genome containing several potential insertion sites and permitting the simultaneous insertion of several expression cassettes for foreign genes. This affords the possibility of vaccinating dogs at the same time against different canine pathogenic agents using a single recombinant virus.

The main objective of the invention is to provide a vaccinal vector permitting the expression of immunogens of canine pathogens for the purpose of protecting dogs against the main canine infectious diseases.

Another objective of the invention is to provide such a vector permitting the vaccination of dogs, and especially puppies having maternal antibodies, via the mucosal, in particular the oral, nasal or conjunctival, route.

Yet another objective of the invention is to provide such a vector which permits vaccination at the same time against herpesvirosis in puppies.

Hence the subject of the present invention is a recombinant live vaccine using as vector a canine herpesvirus comprising and expressing at least one nucleotide sequence coding for a polypeptide, this sequence being inserted into a site which is non-essential for replication in vitro.

The inventors have isolated and analysed a genomic fragment of the CHV virus, on which they have characterized 5 open reading frames (ORF1 to ORF5), among which two (ORF3 and ORF5) have proved to be non-essential for replication in vitro. Moreover, the inventors have found that other regions of the CHV genome could also be used to insert foreign genes. These insertion sites are: thymidine kinase gene (CHV TK ORF) (Rémond M. et al. Virus Research. 1995. 39. 341–354.) and sequence situated between the CHV ORF19 and the CHV ORF22 (Rémond M. et al. J. Gen. Virol. 1996. 76. 37–48). These sites are described more precisely in the examples of the present invention.

Preferably, the inserted sequence codes for an antigenic polypeptide, and preferentially for an antigenic polypeptide of a canine pathogenic agent. It is also possible to insert the sequences coding for immunomodulatory proteins such as cytokines. According to an advantageous variant, it is possible to use in combination a sequence coding for a cytokine, or the like, and a sequence coding for an antigen. If need be, several cytokine sequences can be used in combination with one another, optionally in combination with one or more sequences coding for antigens.

The insertion into the sites is carried out by simple insertion (without deletion), or after partial or total deletion of the ORF or ORFs used as insertion sites.

As a parent virus for the construction of recombinant CHV viruses, it is possible to use, in particular, the CHV strain F205 which was isolated by L. Carmichael (Proc. Soc. Exp. Biol. Med. 1965. 120. 644–650).

For the expression of foreign genes inserted into the CHV genome according to the present invention, it will be preferable to use a strong eukaryotic promoter such as, preferentially, a cytomegalovirus (CMV) immediate-early (IE) promoter. CMV IE promoter is understood to mean, in particular, a fragment such as is given in the examples, as well as the subfragments thereof retaining the same promoter activity. The CMV IE promoter can be the human (HCMV IE) promoter or the murine (MCMV IE) promoter, or alternatively a CMV IE promoter of another origin, for example rat, guinea pig or porcine CMV.

At least two nucleotide sequences may be inserted into one site under the control of different promoters. The latter may be, in particular, CMV IE promoters of different origins.

According to an advantageous development of the invention, another promoter is used in combination with the CMV IE promoter in such a way that the two promoters have their 5' ends adjacent and that the transcriptions initiated from these two promoters take place in opposite directions. This particular arrangement enables two nucleotide sequences to be inserted into the same site, one under the control of the CMV IE promoter and the other under that of the promoter used in combination with it. This construction is noteworthy from the fact that the presence of the CMV IE promoter, and in particular of its enhancer portion, can activate the transcription induced by the promoter used in combination. As a promoter used in combination, there may be mentioned, for example, a CMV promoter of different species from the first promoter. It is also possible to envisage other promoters, such as the Marek's disease virus (MDV) RNA1.8 promoter (G. Bradley et al. J. Virol. 1989. 63. 2534–2542).

The nucleotide sequence inserted into the CHV vector in order to be expressed can be any sequence coding for an antigenic polypeptide of a canine pathogenic agent capable, when expressed under the favourable conditions obtained by the invention, of bringing about an immunization leading to an effective protection of the vaccinated animal against the pathogenic agent. The nucleotide sequences coding for the antigens of interest for a given disease, in particular the viral, bacterial or parasitic diseases mentioned above, may hence be inserted under the conditions described by the present invention.

The typical case of the invention is the insertion of at least one nucleotide sequence coding appropriately for a polypeptide of the Carré's disease virus (canine distemper virus=CDV), and preferably for the CDV polypeptide HA (Sidhu M. et al., Virology. 1993. 193. 66–72) or for the CDV polypeptide F (Barrett T. et al. Virus Research. 1987. 8. 373–386). It is also possible to insert both of these genes together into the CHV vector. A recombinant live vaccine bringing about protection against Carré's disease is thereby obtained.

Other preferred cases of the invention are the insertion of nucleotide sequences coding for antigens or fragments of antigens of the rabies virus, especially the G gene (Patents FR-A-2,515,685 and EP-A-162,757), of the canine parvovirosis virus (VP2 gene) (Parrish C. et al. J. Virol. 1991. 65. 6544–6552) or of the parainfluenza virus type 2 (HA and/or F genes). It is also possible to insert sequences coding for *Borrelia burgdorferi* antigens, especially the genes coding for the OspA and OspB antigens (Bergström S. et al. Mol. Microbiol. 1989. 3. 479–486).

A typical case of the invention is a vaccine comprising a nucleotide sequence coding for an antigen of the Carré's disease virus under the control of CMV IE, and a nucleotide sequence coding for an antigen of another canine viral disease, in particular the ones mentioned above, under the control of the other promoter.

Naturally, the heterologous sequences and their associated promoters may be inserted more conventionally in tandem into the insertion locus, that is to say according to the same transcription direction.

The expression of several heterologous genes inserted into the insertion locus can also be possible by insertion of a sequence known as an "IRES" (internal ribosome entry site) originating, in particular, from a picornavirus such as the swine vesicular disease virus (SVDV; B. -F. Chen et al., *J. Virology*, 1993, 67, 2142–2148), the encephalomyocarditis virus (EMCV; R. J. Kaufman et al., *Nucleic Acids Research*, 1991, 19, 4485–4490) or the aphthous fever virus (FMDV; N. Luz and E. Beck, *J. Virology*, 1991, 65, 6486–6494), or alternatively of another origin. The content of these three papers is incorporated by reference. The cassette for expression of two genes would hence have the following minimum structure: promoter—gene 1—IRES—gene 2—polyadenylation signal. The recombinant live vaccine according to the invention may hence comprise, inserted into the insertion locus, an expression cassette comprising in succession a promoter, two or more genes separated in pairs by an IRES, and a polyadenylation signal.

In addition to the insertion into the locus according to the invention, it is possible to carry out one or more other insertions, one or more mutations or one or more deletions elsewhere in the genome. In all cases, insertion into a locus other than the one described in the invention enables other genes to be expressed.

The use of the recombinant viruses according to the invention enables dogs to be protected against one or more of the diseases mentioned above, and at the same time against canine herpesvirosis.

The subject of the present invention is also a polyvalent vaccine formula comprising, as a mixture or to be mixed, at least two recombinant live vaccines as defined above, these vaccines comprising different inserted sequences isolated, in particular, from different pathogens. These vaccine formulae contain dosages and/or vehicles which are suited to the administration route.

The subject of the present invention is also CHV viruses modified in at least one of the sites indicated.

Its subject is also a method of vaccination, especially of dogs, in which an effective amount of a vaccine as defined above is administered via any parenteral or mucosal route, but preferably via the mucosal, in particular the oral and/or nasal, route. The vaccinal dose will preferably be between $10^2$ CCID50 and $10^7$ CCID50. Preferably, the dose for the parenteral route will be between $10^4$ CCID50 and $10^7$ CCID50, and for the oral and/or nasal route, between $10^2$ CCID50 and $10^5$ CCID50. As defined, the vaccine is effective in general after a single administration via the oral and/or nasal route. However, repeated administrations may be necessary.

The subject of the present invention is also the DNA fragments comprising all or part of the sequence defined by positions 1 to 6216 on SEQ ID No. 1 (FIG. 1), in particular all or part of the ORF3 site defined and/or of the flanking sequences located upstream and downstream of this site, which fragments will be useful as flanking arms for the techniques of homologous recombination with the genome of the CHV virus chosen as parent virus. Naturally, the invention also relates to the variants of these fragments which correspond to the equivalent sequences of the other strains of CHV. The expert is entirely free to choose the regions serving as flanking arms in connection with the type of insertion (with or without deletion) or of deletion (partial or total) chosen. Generally speaking, the flanking arms may thus have from 100 to 800 base pairs, but can be larger if necessary.

A further subject of the invention is a method of preparation of the vectors and vaccines according to the invention, as emerges from the description of the vaccines, by insertion of genes of interest into the insertion site.

The invention will now be described in greater detail by means of non-limiting examples of implementation, taken with reference to the drawing, wherein:

FIG. 1: Sequence of the CHV region (6216 base pairs) and translation of the different open reading frames (ORFs) present in this sequence (ORF1 to ORF5).

FIG. 2: Plasmid pPB200 (donor plasmid for the insertion of expression cassettes into the CHV ORF3 site).

Figure 3:
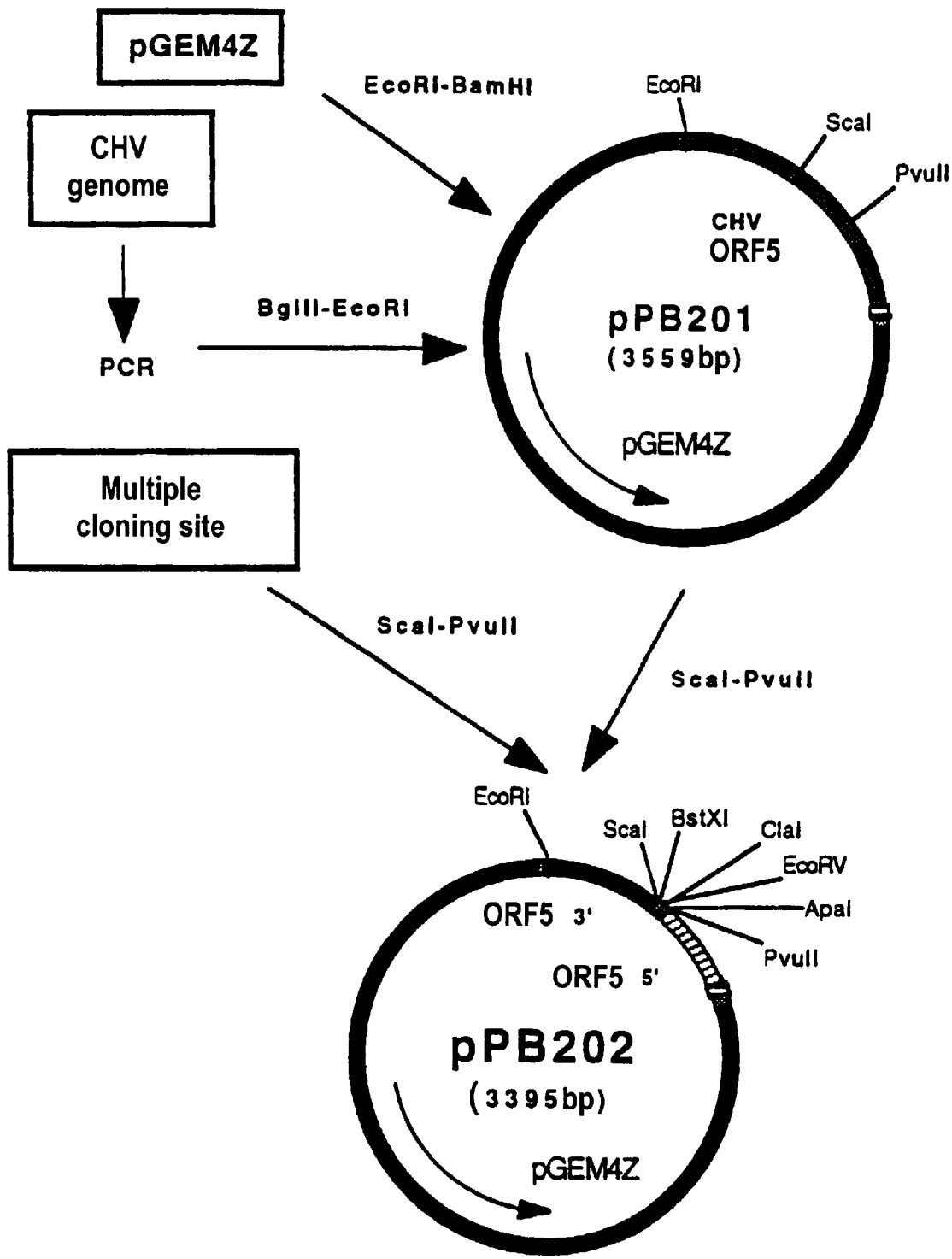

FIG. 3: Construction of the plasmid pPB202 (donor plasmid for the insertion of expression cassettes into the CHV ORF5 site).

Figure 4:
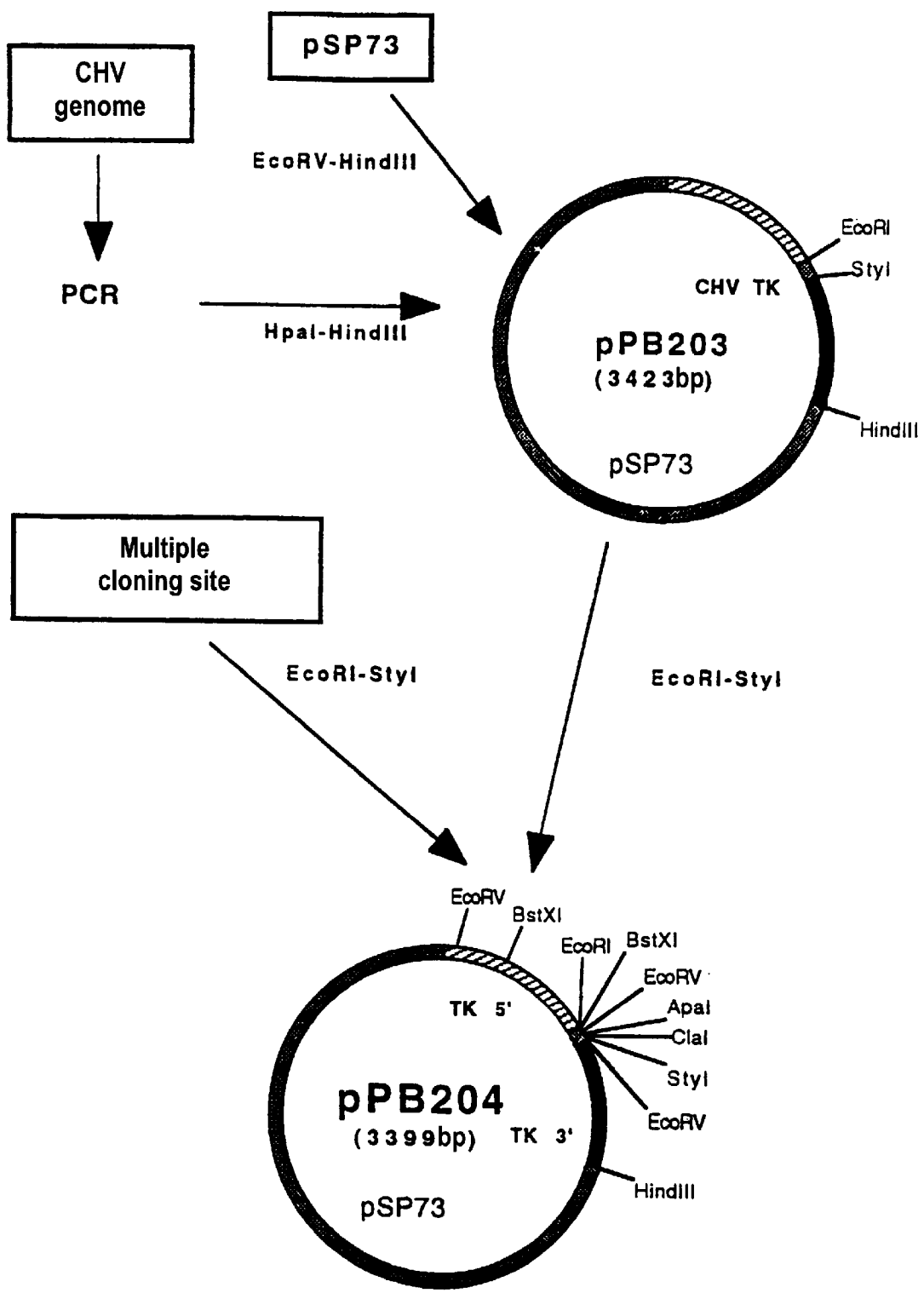

FIG. 4: Construction of the plasmid pPB204 (donor plasmid for the insertion of expression cassettes into the CHV TK site).

Figure 5:
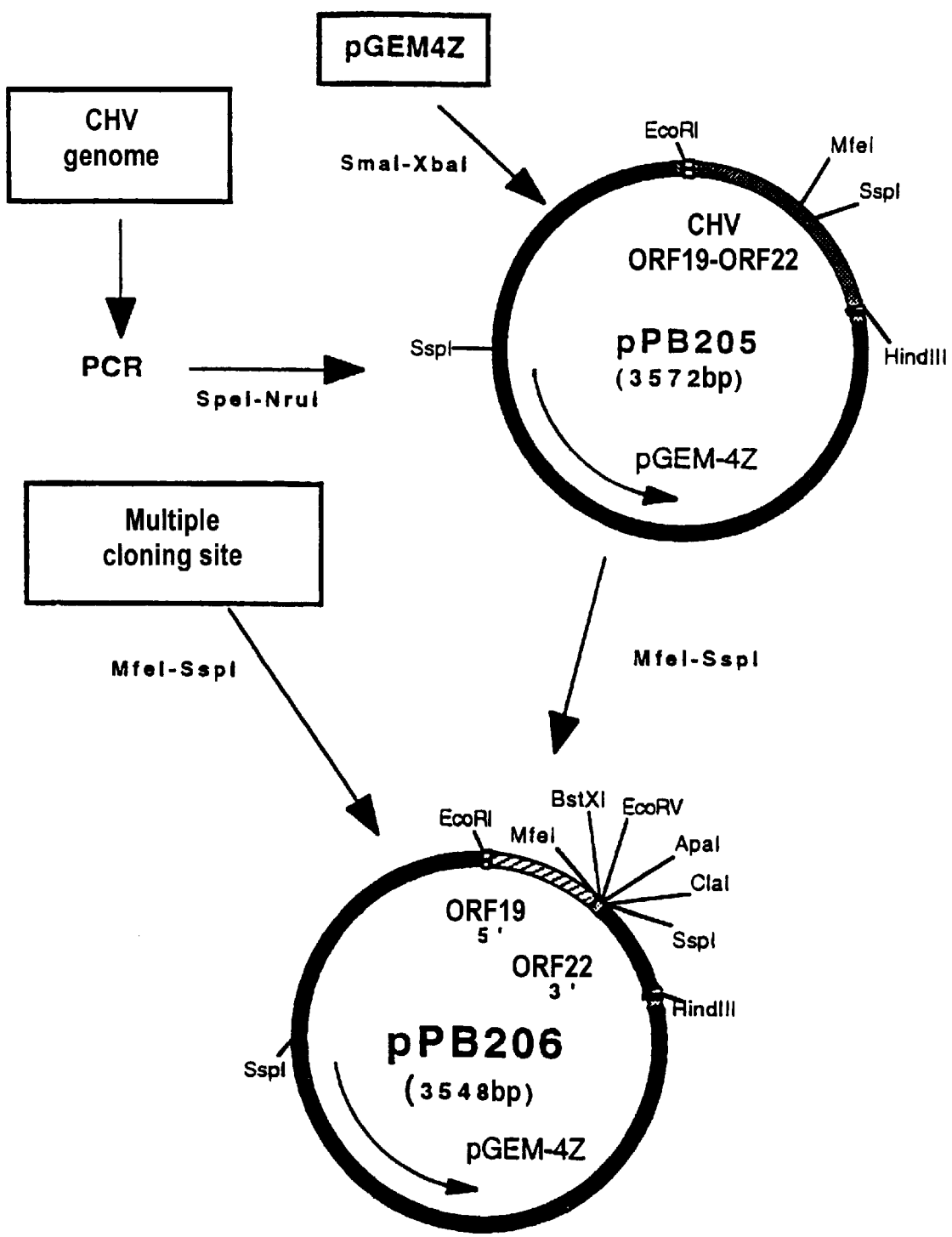

FIG. 5: Construction of the plasmid pPB206 (donor plasmid for the insertion of expression cassettes into the site situated between the CHV ORF19 and CHV ORF22 genes).

Figure 6:
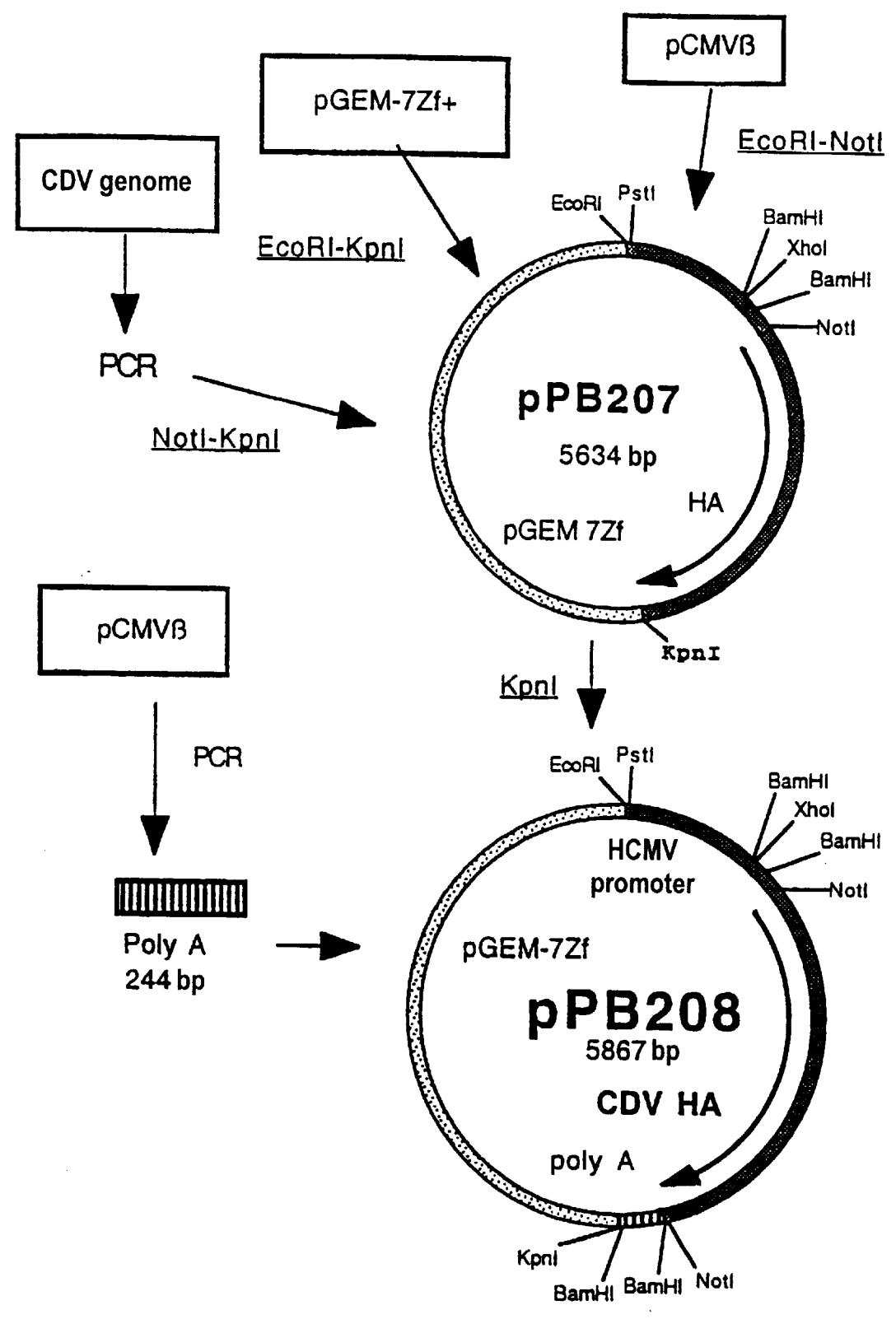

FIG. 6: Construction of the plasmid pPB208 (expression cassette for the CDV HA gene).

Figure 7:
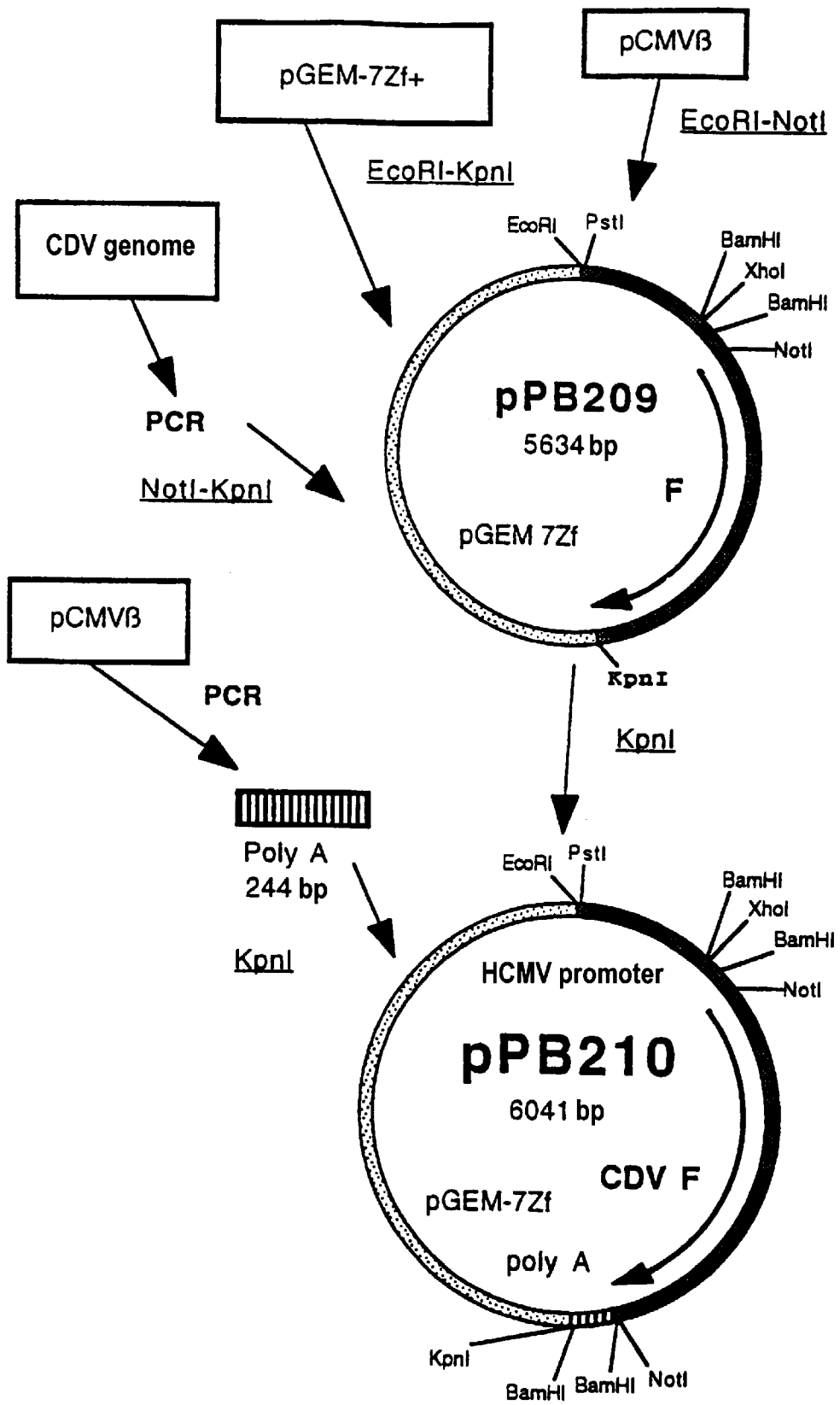

FIG. 7: Construction of the plasmid pPB210 (expression cassette for the CDV F gene).

Figure 8:
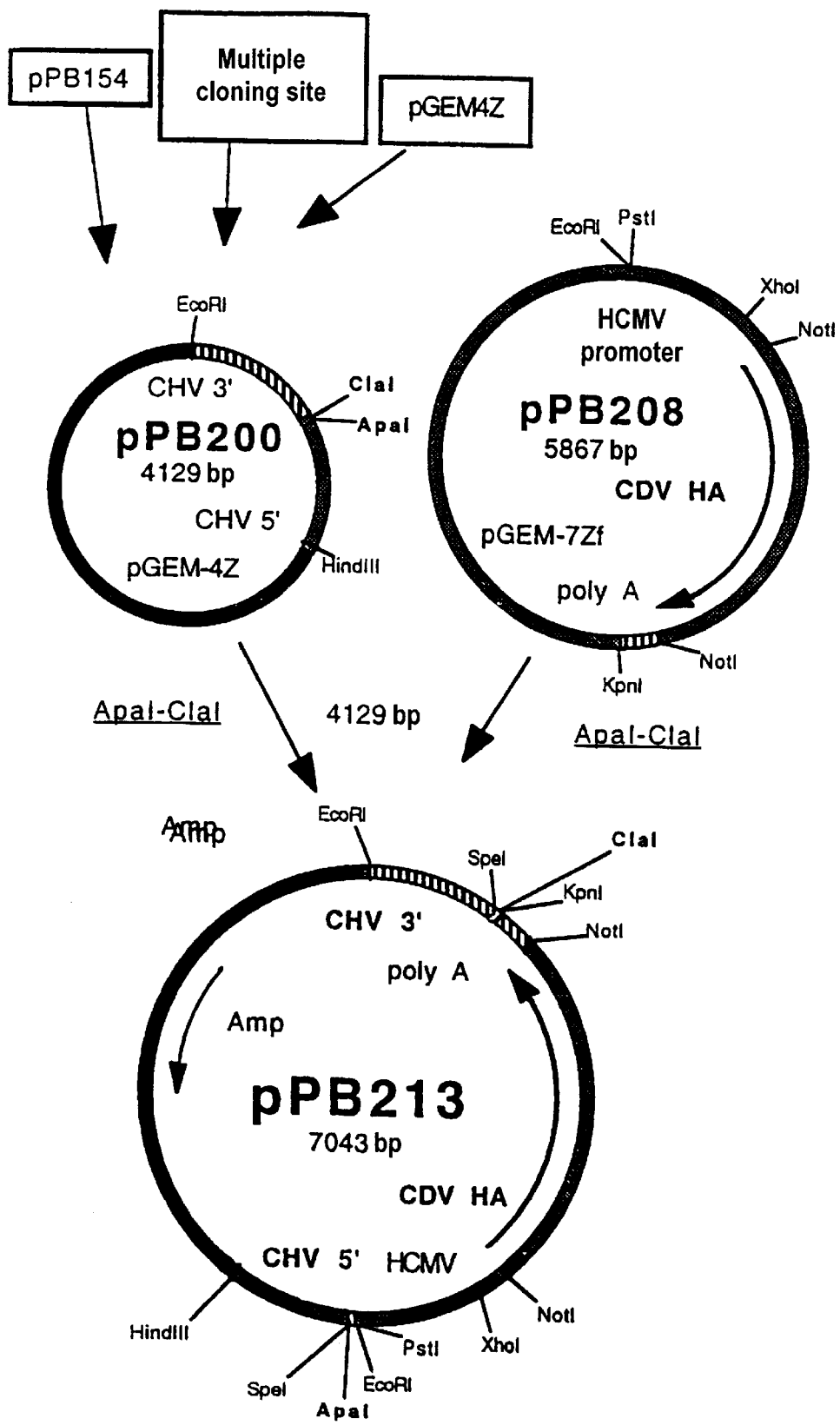

FIG. 8: Construction of the plasmid pPB213 (donor plasmid for the insertion of the cassette for the expression of the CDV HA gene into the CHV ORF3 site).

Figure 9:
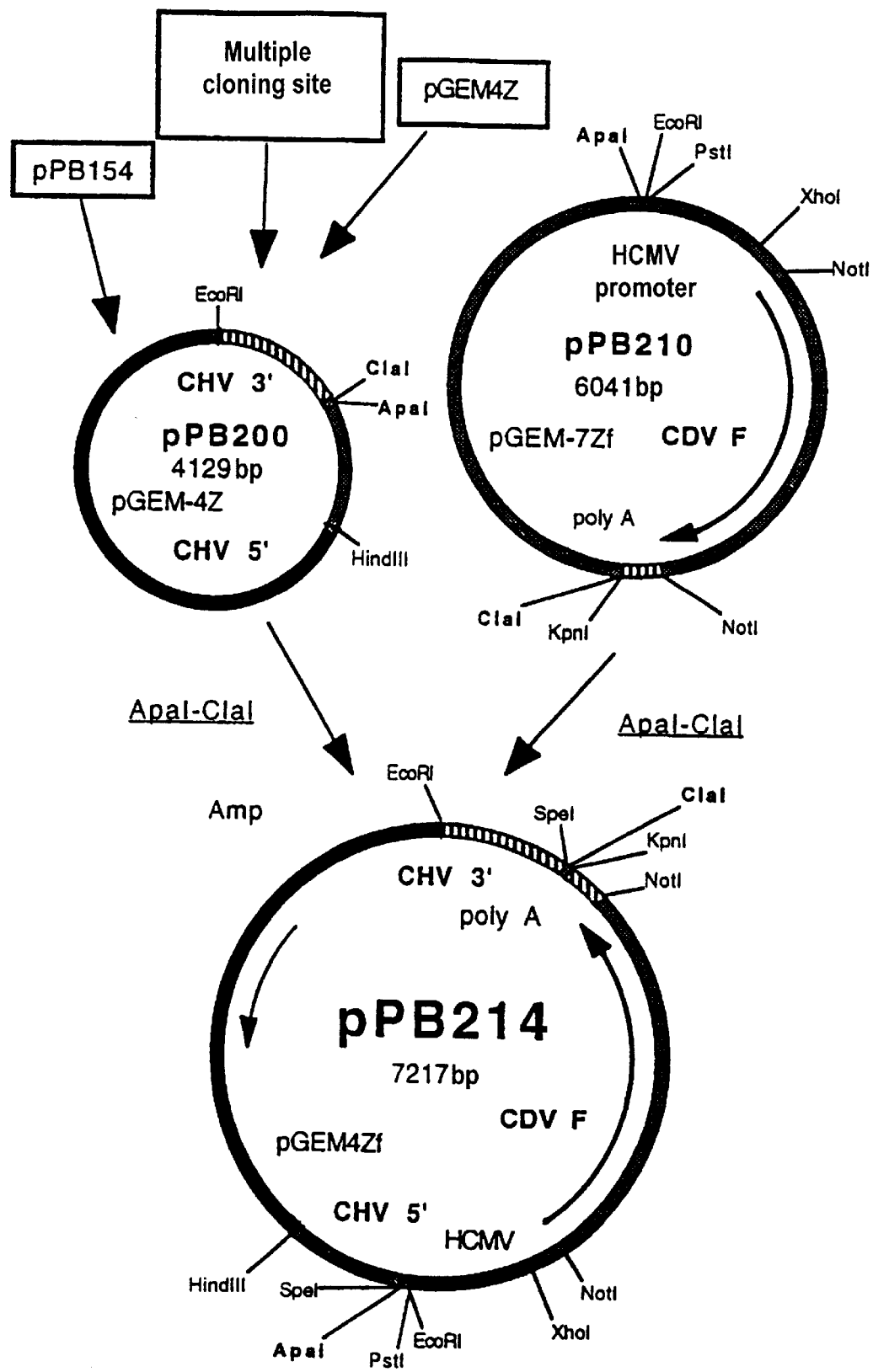

FIG. 9: Construction of the plasmid pPB214 (donor plasmid for the insertion of the cassette for the expression of the CDV F gene into the CHV ORF3 site).

FIG. 10: Plasmid pPB200'

FIG. 11: Construction of the plasmid pPB212 (cassette for the expression of the rabies virus G gene).

FIG. 12: Construction of the plasmid pPB125 (donor plasmid for the insertion of the cassette for the expression of the rabies virus G gene into the CHV ORF3 site).

FIG. 13: Construction of the plasmid pPB216 (donor plasmid for the insertion of the cassette for the expression of the CDV HA gene into the CHV ORF5 site).

FIG. 14: Construction of the plasmid pPB217 (donor plasmid for the insertion of the cassette for the expression of the CDV HA gene into the CHV TK site).

FIG. 15: Construction of the plasmid pPB218 (donor plasmid for the insertion of the cassette for the expression of the CDV HA gene into the site situated between the CHV ORF19 and CHV ORF22 genes).

SEQ ID sequence listing for the constructions in the insertion sites of the CHV vector:

| | |
|---|---|
| SEQ ID Nos. 1 and 2 | Complete sequence of the CHV ORF1 → ORF5 region depicted in FIG. 1 |
| SEQ ID No. 3 | ORF1 amino acid sequence of FIG. 1 |
| SEQ ID No. 4 | ORF2 amino acid sequence of FIG. 1 |
| SEQ ID No. 5 | ORF3 amino acid sequence of FIG. 1 |
| SEQ ID No. 6 | ORF4 amino acid sequence of FIG. 1 |
| SEQ ID No. 7 | (Partial) ORF5 amino acid sequence of FIG. 1 |
| SEQ ID No. 8 | Oligonucleotide JCA070 |
| SEQ ID No. 9 | Oligonucleotide JCA071 |
| SEQ ID No. 10 | Oligonucleotide JCA072 |
| SEQ ID No. 11 | Oligonucleotide JCA073 |
| SEQ ID No. 12 | Oligonucleotide JCA074 |
| SEQ ID No. 13 | Oligonucleotide JCA075 |
| SEQ ID No. 14 | Oligonucleotide JCA076 |
| SEQ ID No. 15 | Oligonucleotide JCA077 |
| SEQ ID No. 16 | Oligonucleotide JCA078 |
| SEQ ID No. 17 | Oligonucleotide JCA079 |
| SEQ ID No. 18 | Oligonucleotide JCA080 |
| SEQ ID No. 19 | Oligonucleotide JCA081 |
| SEQ ID No. 20 | Oligonucleotide JCA082 |
| SEQ ID No. 21 | Oligonucleotide JCA083 |
| SEQ ID No. 22 | Oligonucleotide JCA084 |
| SEQ ID No. 23 | Oligonucleotide JCA085 |
| SEQ ID No. 24 | Oligonucleotide PB088 |
| SEQ ID No. 25 | Oligonucleotide PB089 |
| SEQ ID No. 26 | Oligonucleotide JCA086 |
| SEQ ID No. 27 | Oligonucleotide JCA087 |
| SEQ ID No. 28 | Oligonucleotide JCA088 |
| SEQ ID No. 29 | Oligonucleotide JCA089 |
| SEQ ID No. 30 | Oligonucleotide JCA090 |
| SEQ ID No. 31 | Oligonucleotide JCA091 |

EXAMPLES

All the constructions of plasmids were carried out using the standard techniques of molecular biology described by Sambrook J. et al. (*Molecular Cloning: A Laboratory Manual.* $2^{nd}$ Edition. Cold Spring Harbor Laboratory. Cold Spring Harbor. New York. 1989). All the restriction fragments used for the present invention were isolated using the "Geneclean" kit (BIO 101 Inc. La Jolla, Calif.).

The virus used as parent virus is the canine herpesvirus strain F205 (also known as the Carmichael strain). This strain was obtained from Dr. L. Carmichael (Cornell University, N.Y.), who isolated it and described its biological characteristics (Proc. Soc. Exp. Biol. Med. 1965. 120. 644–650). The conditions of culture of this virus are as follows: MDCK (Madin-Darby canine kidney ATCC CCL34) cells cultured in Eagle's minimum essential medium (MEM medium) are inoculated with the CHV strain F205 using a multiplicity of infection of 1. The infected cells are then incubated at 37° C. for approximately 36 hours until a complete cytopathic effect is seen.

Example 1: Extraction of canine herpesvirus DNA

After culture, the supernatant and the lysed cells are harvested, and the whole of the viral suspension is centrifuged at 1000 g for 10 minutes at +4° C. to remove cell debris. The viral particles are then harvested by ultracentrifugation at 400,000 g for 1 hour at +4° C. The pellet is taken up in a minimum volume of buffer (10 mM Tris, 1 mM EDTA). This concentrated viral suspension is treated with proteinase K (100 μg/ml final) in the presence of sodium dodecyl sulphate (SDS) (0.5% final) for 2 hours at 37° C. The viral DNA is then extracted with a phenol/chloroform mixture and thereafter precipitated with 2 volumes of absolute ethanol. After one night at −20° C., the precipitated DNA is centrifuged at 10,000 g for 15 minutes at +4° C. The DNA pellet is dried and then taken up in a minimum volume of sterile ultrapure water.

Example 2: Cloning and characterization of the CHV ORF1–ORF5 region

The purified genomic DNA of the CHV virus strain F205 was digested with the restriction enzymes ScaI and XhoI, and the approximately 6200-bp ScaI-XhoI fragment was cloned into the vector pBlueScript SKII+ (Stratagene Ref. 212205), previously digested with ScaI and XhoI, to give the plasmid pPB154.

The XhoI-ScaI fragment cloned into plasmid pPB154 was sequenced completely on both strands to generate the 6216-bp sequence of FIG. 1 (SEQ ID No.1and 2).

Several open reading frames larger than 65 amino acids in size were identified on this sequence (FIG. 1):

The first reading frame (ORF1) (positions 1353–157) occurs on the complementary strand and codes for a polypeptide of 398 amino acids (SEQ ID No. 3).

The second reading frame (ORF2) (positions 1708–2970) codes for a polypeptide of 420 amino acids (SEQ ID No. 4).

The third reading frame (ORF3) (positions 3040–4242) codes for a polypeptide of 400 amino acids (SEQ ID No. 5).

The fourth reading frame (ORF4) (positions 4374–5753) codes for a polypeptide of 459 amino acids (SEQ ID No. 6).

The fifth reading frame (ORF5) (positions 5872–6216) is incomplete and codes for a truncated protein of 115 amino acids (SEQ ID No. 7).

The different open reading frames are collated in the table below:

| Open reading frame | Beginning–End (positions in FIG. 1) | Size in amino acids |
|---|---|---|
| ORF 1 | 1353–157 | 398 aa |
| ORF 2 | 1708–2970 | 420 aa |
| ORF 3 | 3040–4242 | 400 aa |
| ORF 4 | 4374–5753 | 459 aa |
| ORF 5 | 5872–6216 | 115 aa |

Example 3: Construction of plasmid pPB200 for the insertion of expression cassettes into the CHV ORF3 site (FIG. 2)

Plasmid pPB154 (9121 bp) (Example 2) was digested with HindIII and SpeI to isolate the 620-bp HindIII-SpeI fragment (fragment A). Plasmid pPB154 was digested with EcoRI and SpeI to isolate the 659-bp EcoRI-SpeI fragment (fragment B). The fragments A and B were ligated together with the vector pGEM4Z (Promega Ref. P2161), previously digested with EcoRI and HindIII, to give the plasmid pPB199 (4096 bp). Plasmid pPB199 was then digested with SpeI, treated with alkaline phosphatase and then ligated with the multiple cloning site obtained by hybridization of the following 2 oligonucleotides:
JCA070 (33 mer) (SEQ ID No. 8) 5' CTAGTCCAGCAAGGTGGATCGATATCGGGCCCA 3'
JCA071 (33 mer) (SEQ ID No. 9) 5' CTAGTGGGCCCGATATCGATCCACCTTGCTGGA 3'
to give plasmid pPB200 (4129 bp).

Example 4: Construction of plasmid pPB202 for the insertion of expression cassettes into the CHV ORF5 site (FIG. 3)

The sequence of the CHV ORF5 gene was published recently (Limbach K. et al. J. Gen. Virol. 1994. 75. 2029–2039). A PCR reaction was carried out with the genomic DNA of the CHV virus strain F205 (Example 1) and with the following oligonucleotides:
JCA072 (22 mer) (SEQ ID No. 10) 5' CAGCTTTATGTTTTTATTGTTC 3'
JCA073 (29 mer) (SEQ ID No. 11) 5' AAAGAATTCTACAACTGTTTAATAAAGAC 3'
to obtain a 751-bp PCR fragment containing the complete CHV ORF2 gene. This fragment was digested with BGlII and EcoRI to isolate a 709-bp BglII-EcoRI fragment. This fragment was ligated with the vector pGEM4Z (Promega Ref. P2161), previously digested with EcoRI and BanHI, to give the plasmid pPB201 (3559 bp). Plasmid pPB201 was then digested with ScaI and PvuII and thereafter ligated with a multiple cloning site obtained by hybridization of the following 2 oligonucleotides:
JCA074 (36 mer) (SEQ ID No. 12) 5' ACTCCAGCTACATGGGATATCGGGCCCATCGATCAG 3'
JCA075 (36 mer) (SEQ ID No. 13) 5' CTGATCGATGGGCCCGATATCCCATGTAGCTGGAGT 3'
to give plasmid pPB202 (3395 bp).

Example 5: Construction of plasmid pPB204 for the insertion of expression cassettes into the CHV TK site (FIG. 4)

The sequence of the CHV thymidine kinase (TK) gene was published recently (Rémond M. et al. Virus Research. 1995. 39. 341–354). A PCR reaction was carried out with the genomic DNA of the CHV virus strain F205 (Example 1) and with the following oligonucleotides:
JCA076 (35 mer) (SEQ ID No. 14) 5' AGCGTTAACCTCAAAAGCCAAATTTACACTTCCCG 3'
JCA077 (38 mer) (SEQ ID No. 15) 5' CCCAAGCTTTTCTAAAGCCCATTTATAAATAATAAATG 3'
to obtain a 1030-bp PCR fragment containing the thymidine kinase (TK) gene. This fragment was digested with HpaI and HindIII to isolate a 1019-bp HpaI-HindIII fragment. This fragment was ligated with the vector pSP73 (Promega Ref. P2221), previously digested with EcoRV and HindIII, to give the plasmid pPB203 (3423 bp).

Plasmid pPB203 was then digested with EcoRI and StyI and thereafter ligated with a multiple cloning site obtained by hybridization of the following 2 oligonucleotides:
JCA078 (36 mer) (SEQ ID No. 16) 5' AATTCCCAGCTACATGGGATATCGGGCCCATCGATC 3'
JCA079 (36 mer) (SEQ ID No. 17) 5' CAAGGATCGATGGGCCCGATATCCCATGTAGCTGGG 3'
to give plasmid pPB204 (3399 bp).

Example 6: Construction of plasmid pPB206 for the insertion of expression cassettes into the site situated between the CHV ORF19 and ORF22 genes (FIG. 5)

The sequence of the intergenic region corresponding to the natural deletion of the genes coding for the large subunit ("RR1" gene) and for the small subunit ("RR2" gene) of ribonucleotide reductase was published recently (Rémond M. et al. J. Gen. Virol. 1996, 77. 37–48). According to the nomenclature used by Rémond et al., the deletion of these two genes occurs between the open reading frames designated CHV "orf19" and CHV "orf22" [designated herein ORF19 and ORF 22, respectively]. A PCR reaction was carried out with the genomic DNA of the CHV virus strain F205 (Example 1) and with the following oligonucleotides:
JCA080 (36 mer) (SEQ ID No. 18) 5' GGAGATCTAGTAAATTAAATAGTAATTCATTTAATG 3'
JCA081 (33 mer) (SEQ ID No. 19) 5' CAGTCGCGAAGATGAAAATAAAATCCATCGAAG 3'
to obtain a 720-bp PCR fragment containing the intergenic region corresponding to the natural deletion of the CHV ORF19 and ORF22 genes. This fragment was digested with SpeI and NruI to isolate a 709-bp SpeI-NruI fragment. This fragment was ligated with the vector pGEM4Z (Promega Ref. P2161), previously digested with SmaI and XbaI, to give the plasmid pPB205 (3572 bp). Plasmid pPB205 was then digested with MfeI and thereafter partially digested with SspI in order to isolate the 3512-bp MfeI-SspI fragment. This fragment was then ligated with a multiple cloning site obtained by hybridization of the following 2 oligonucleotides:
JCA082 (38 mer) (SEQ ID No. 20) 5' AATTGGCAGCTACATGGGATATCGGGCCCATCGATAAT 3'
JCA083 (34 mer) (SEQ ID No. 21) 5' ATTATCGATGGGCCCGATATCGGATGTAGCTGGC 3'
to give plasmid pPB206 (3548 bp).

Example 7: Isolation of the genomic RNA of the CDV strain Onderstepoort and cloning of the complementary DNA coding for the HA and F genes The CDV strain Onderstepoort (Mitchell W. et al. J. Virol. Meth. 1987. 18. 121–131) was cultured on MDCK (Madin-Darby canine kidney) cells in DMEM medium (Gibco). After purification of the virus, the genomic viral RNA was isolated using the guanidinium thiocyanate/phenol-chloroform extraction technique (Chomczynski P. and Sacchi N., Anal. Biochem. 1987. 162. 156–159). Specific oligonucleotides (containing restriction sites at their 5' ends to facilitate the cloning of the amplified fragments) were synthesized in such a way as to cover completely the coding regions of the genes which were to be amplified (HA and F genes, respectively). The reverse transcription (RT) reaction and polymerase chain amplification (PCR) were performed according to the standard techniques (Sambrook J. et al. 1989). Each RT-PCR reaction was carried out with a pair of specific amplimers and taking as template the extracted viral genomic RNA. The amplified complementary DNA was extracted with phenol/chloro-form/isoamyl alcohol (25:24:1) before being digested with the restriction enzymes and cloned into the appropriate vector.

7.1. Construction of the CDV HA expression cassette (pPB208) (FIG. 6)

The plasmid pCMVB (Clontech Ref. 6177-1) was digested with EcoRI and NotI to isolate an 818-bp EcoRI-NotI fragment containing the promoter region of the human cytomegalovirus immediate-early gene (fragment A).

An RT-PCR reaction was carried out with the genomic RNA of the CDV virus (strain Onderstepoort) and with the following oligonucleotides:

JCA084 (32 mer) (SEQ ID No. 22) 5' TTGCGGCCGCATGCTCCCCTACCAAGACAAGG 3'

JCA085 (28 mer) (SEQ ID No. 23) 5' TTGGTACCTTAACGGTTACATGAGAATC 3' to obtain a 1837-bp PCR fragment containing the CDV HA gene. This fragment was digested with NotI and KpnI to isolate a 1826-bp NotI-KpnI fragment (fragment B).

The fragments A and B were ligated together with the vector pGEM-7Zf+ (Promega Cat #P2251), previously digested with EcoRI and KpnI, to give the plasmid pPB207 (5634 bp).

A PCR reaction was carried out with plasmid pCMVB and with the following oligonucleotides:
PB088 (30 mer) (SEQ ID No. 24) 5' TTGGGTACCGC-CTCGACTCTAGGCGGCCGC 3'
PB089 (32 mer) (SEQ ID No. 25) 5' TTGGGTACCGGATC-CGAAAAAACCTCCCACAC 3'
to obtain a 244-bp PCR fragment containing the polyadenylation signal of the SV40 virus early gene. This fragment was digested with KpnI to isolate a 233-bp KpnI-KpnI fragment. This fragment was then ligated with plasmid pPB207, previously digested with KpnI, to give plasmid pPB208 (5867 bp).

7.2. Construction of the CDV F expression cassette (pPB210) (FIG. 7)

Plasmid pCMVB (Clontech Ref. 6177-1) was digested with EcoRI and NotI to isolate an 818-bp EcoRI-NotI fragment containing the promoter region of the human cytomegalovirus immediate-early gene (fragment A).

An RT-PCR reaction was carried out with the genomic RNA of the CDV virus (strain Onderstepoort) and with the following oligonucleotides:
JCA086 (34 mer) (SEQ ID No. 26) 5' TTGCGGCCGCAT-GCACAGGGGAATCCCCAAAAGC 3'
JCA087 (28 mer) (SEQ ID No. 27) 5' TTGGTACCTCA-GAGTGATCTACATAGG 3'
to obtain a 2011-bp PCR fragment containing the CDV F gene. This fragment was digested with NotI and KpnI to isolate a 2000-bp NotI-KpnI fragment (fragment B). The fragments A and B were ligated together with the vector pGEM-7Zf+ (Promega Ref. P2251), previously digested with EcoRI and KpnI, to give the plasmid pPB209 (5808 bp).

A PCR reaction was carried out with plasmid pCMVB and with the following oligonucleotides:
PB088 (30 mer) (SEQ ID No. 24) 5' TTGGGTACCGC-CTCGACTCTAGGCGGCCGC 3'
PB089 (32 mer) (SEQ ID No. 25) 5' TTGGGTACCGGATC-CGAAAAAACCTCCCACAC 3'
to obtain a 244-bp PCR fragment containing the polyadenylation signal of the SV40 virus early gene. This fragment was digested with KpnI to isolate a 233-bp KpnI-KpnI fragment. This fragment was then ligated with plasmid pPB209, previously digested with KpnI, to give plasmid pPB210 (6041 bp).

Example 8: Construction of the donor plasmid pPB213 for the insertion of the CDV EA expression cassette into the CHV ORF3 site (FIG. 8)

Plasmid pPB208 (Example 7.1.) was digested with ApaI and ClaI to isolate a 2920-bp ApaI-ClaI fragment containing the cassette for the expression of the CDV virus HA gene. This fragment was then ligated with plasmid pPB200 (Example 3), previously digested with ApaI and ClaI, to give plasmid pPB213 (7043 bp). This plasmid permits the insertion of the cassette for the expression of the CDV HA gene into the CHV ORF3 site.

Example 9: Construction of the donor plasmid pPB214 for the insertion of the CDV F expression cassette into the CHV ORF3 site (FIG. 9)

Plasmid pPB210 (Example 7.2.) was digested with ApaI and ClaI to isolate a 3100-bp ApaI-ClaI fragment containing the cassette for the expression of the CDV virus F gene. This fragment was then ligated with plasmid pPB200 (Example 3), previously digested with ApaI and ClaI, to give plasmid pPB214 (7217 bp). This plasmid permits the insertion of the cassette for the expression of the CDV F gene into the CHV ORF3 site.

Figure 10:
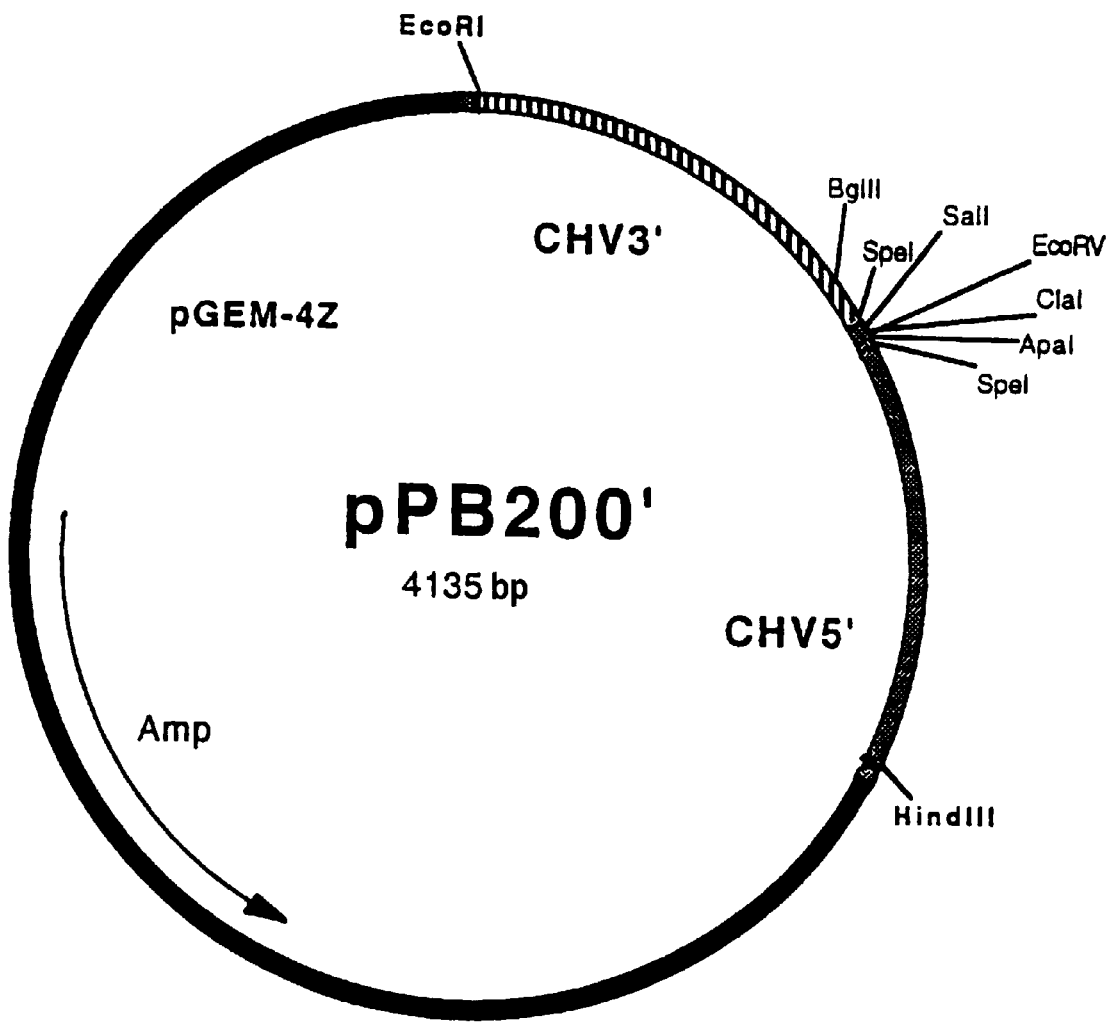
Figure 11:
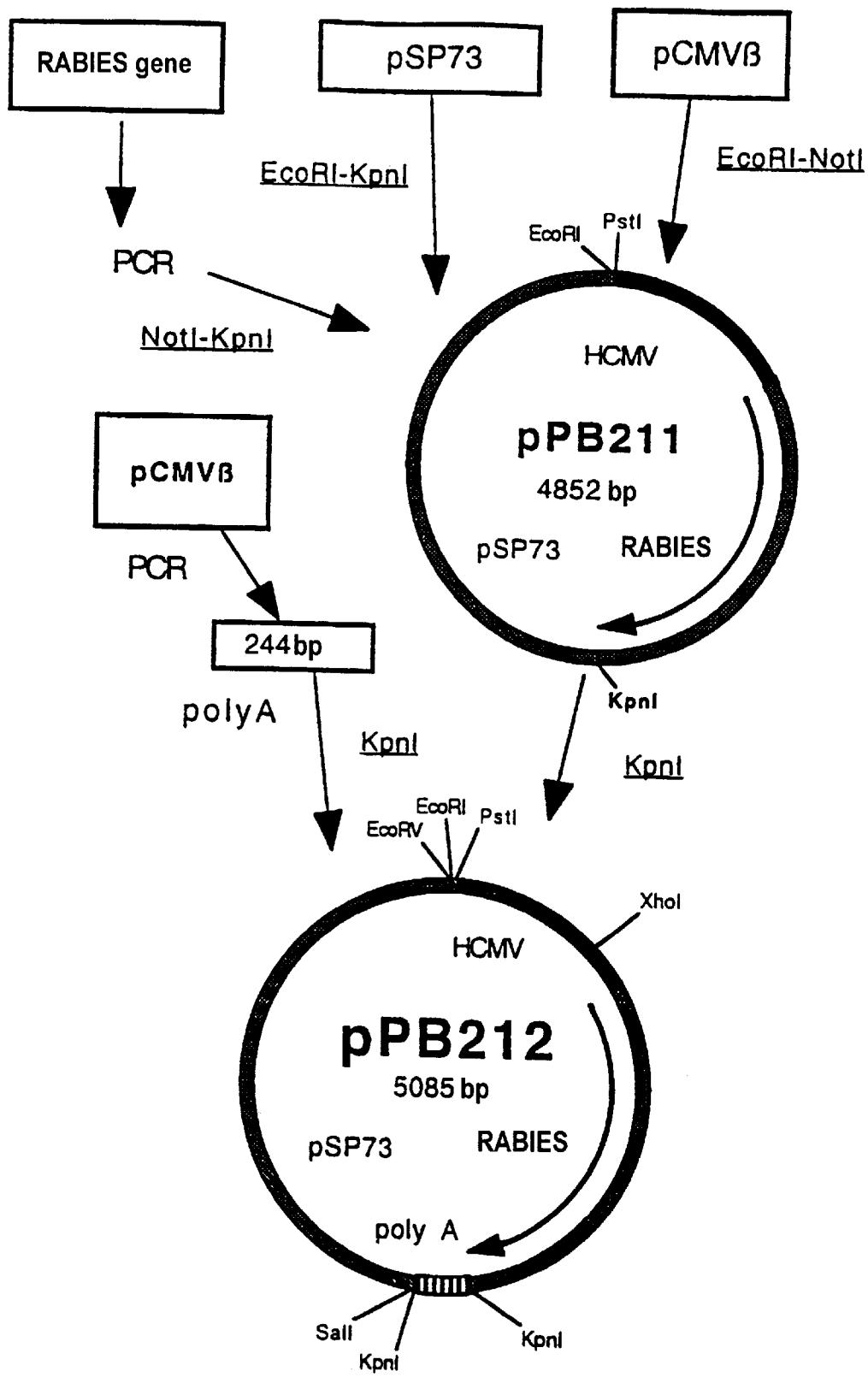
Figure 12:
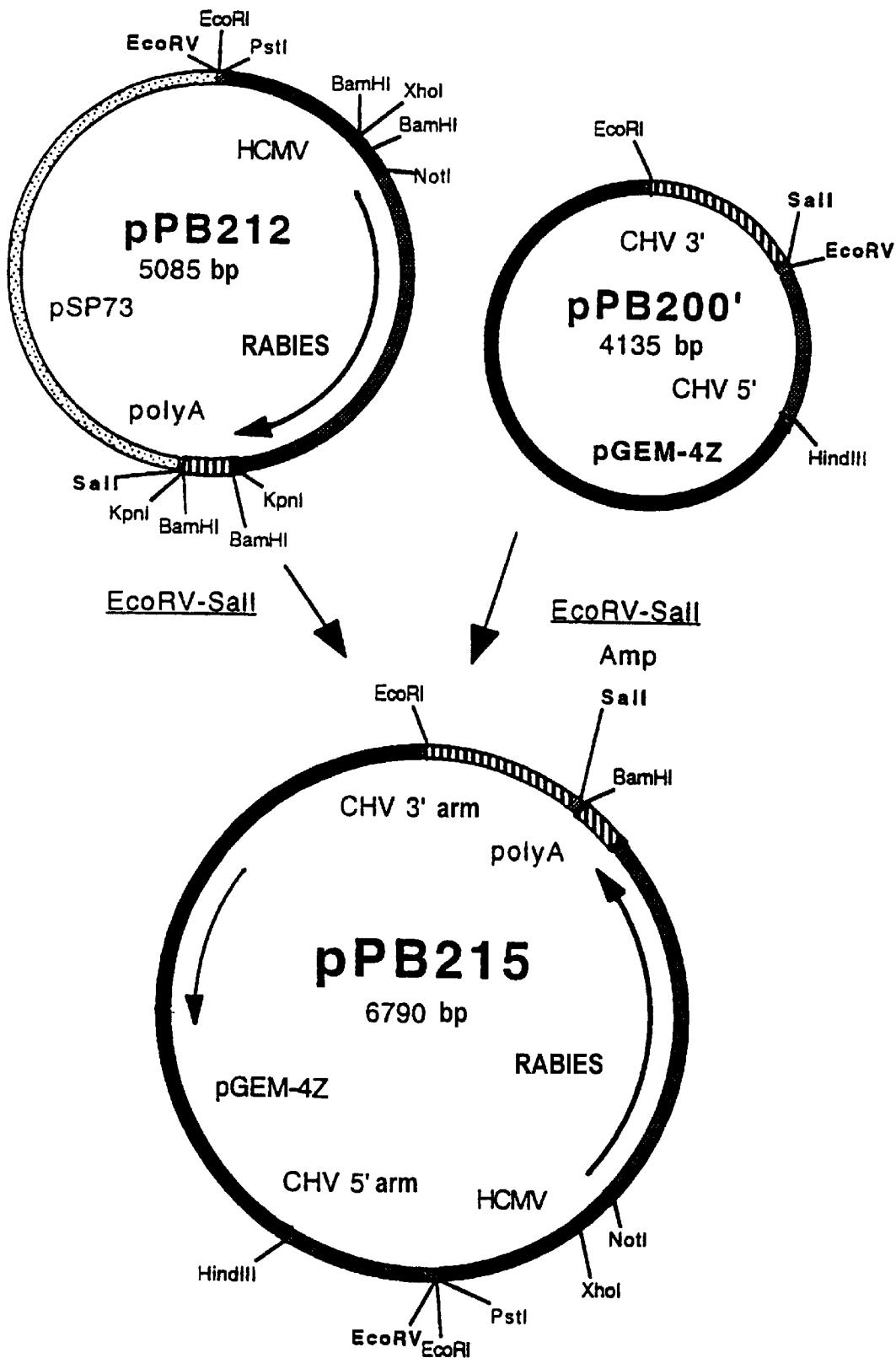

Example 10: Construction of the donor plasmid pPB215 for the insertion of the cassette for the expression of the rabies virus G gene into the CHV ORF3 site (FIGS. 10, 11 and 12)

Plasmid pPB199 (Example 3) was digested with SpeI, treated with alkaline phosphatase and then ligated with the multiple cloning site obtained by hybridization of the following 2 oligonucleotides:
JCA088 (39 mer) (SEQ ID No. 28) 5' CTAGTCCAG-CAAGGTGTCGACGGATCGATATCGGGCCCA 3'
JCA089 (39 mer) (SEQ ID No. 29) 5' CTAGTGGGC-CCGATATCGATCCGTCGACACCTTGCTGGA 3'
to give plasmid pPB200' (4135 bp) (FIG. 10).

Plasmid pCMVB (Clontech Ref. 6177-1) was digested with EcoRI and NotI to isolate an 818-bp EcoRI-NotI fragment containing the promoter region of the human cytomegalovirus immediate-early gene (fragment A).

According to the technical procedures already described for the CDV virus (Example 7), the RNA of the rabies virus ERA strain was extracted and purified from a culture of rabies virus-infected Vero cells. An RT-PCR reaction was then carried out (see Example 7) with the genomic RNA of the rabies virus (strain ERA) and with the following oligonucleotides:
JCA090 (31 mer) (SEQ ID No. 30) 5' TTGCGGCCGCATG-GTTCCTCAGGCTCTCCTG 3'
JCA091 (31 mer) (SEQ ID No. 31) 5' TTGGTACCTCA-CAGTCTGGTCTCACCCCCAC 3'
to obtain a 1597-bp PCR fragment containing the rabies virus G gene (Patents FR-A-2,515,685 and EP-A-162,757). This fragment was digested with NotI and KpnI to isolate a 1586-bp NotI-KpnI fragment (fragment B). The fragments A and B were ligated together with the vector pSP73 (Promega Ref. P2221), previously digested with EcoRI and KpnI, to give the plasmid pPB211 (4852 bp).

A PCR reaction was carried out with plasmid pCMVB and with the following oligonucleotides:
PB088 (30 mer) (SEQ ID No. 24) 5'TTGGGTACCGCCTC-GACTCTAGGCGGCCGC 3'
PB089 (32 mer) (SEQ ID No. 25) 5'TTGGGTACCGGATC-CGAAAAAACCTCCCACAC 3'
to obtain a 244-bp PCR fragment containing the polyadenylation signal of the SV40 virus early gene. This fragment was digested with KpnI to isolate a 233-bp KpnI-KpnI fragment. This fragment was then ligated with plasmid pPB211, previously digested with KpnI, to give plasmid pPB212 (5085 bp) (FIG. 11). Plasmid pPB212 was digested with EcoRV and SalI to isolate a 2664-bp EcoRV-SalI fragment containing the cassette for the expression of the rabies virus G gene. This fragment was then ligated with plasmid pPB200' (see above), previously digested with EcoRV and SalI, to give plasmid pPB215 (6790 bp) (FIG. 12).

Figure 13:
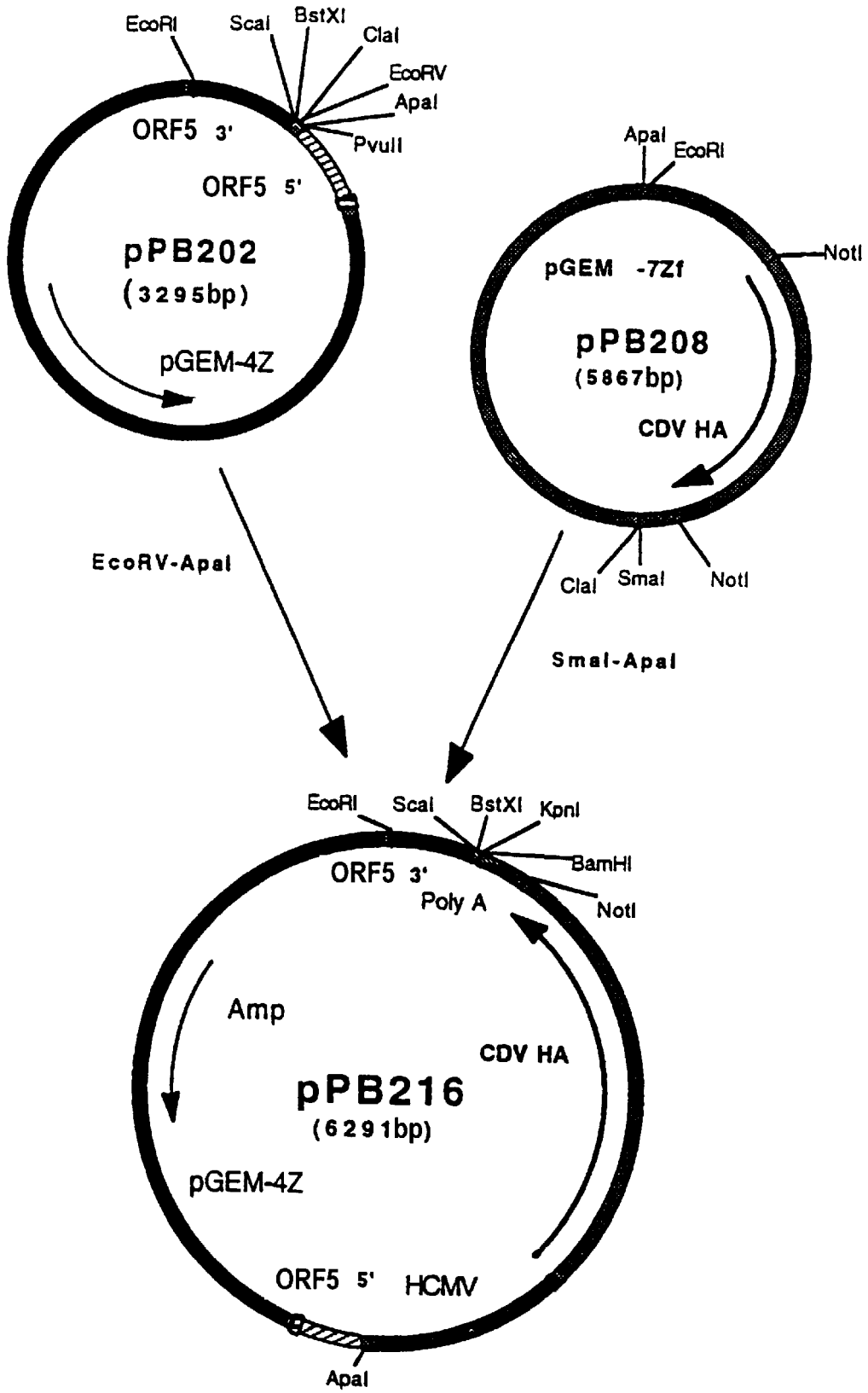

Example 11: Construction of the donor plasmid pPB216 for the insertion of the CDV HA expression cassette into the CHV ORF5 site (FIG. 13)

Plasmid pPB208 (Example 7.1.) was digested with SmaI and ApaI to isolate a 2909-bp SmaI-ApaI fragment containing the cassette for the expression of the CDV HA gene. This fragment was then ligated with plasmid pPB202 (Example 4), previously digested with EcoRV and ApaI, to give plasmid pPB216 (6291 bp). This plasmid permits the insertion of the cassette for the expression of the CDV HA gene into the CHV ORF5 site.

Figure 14:
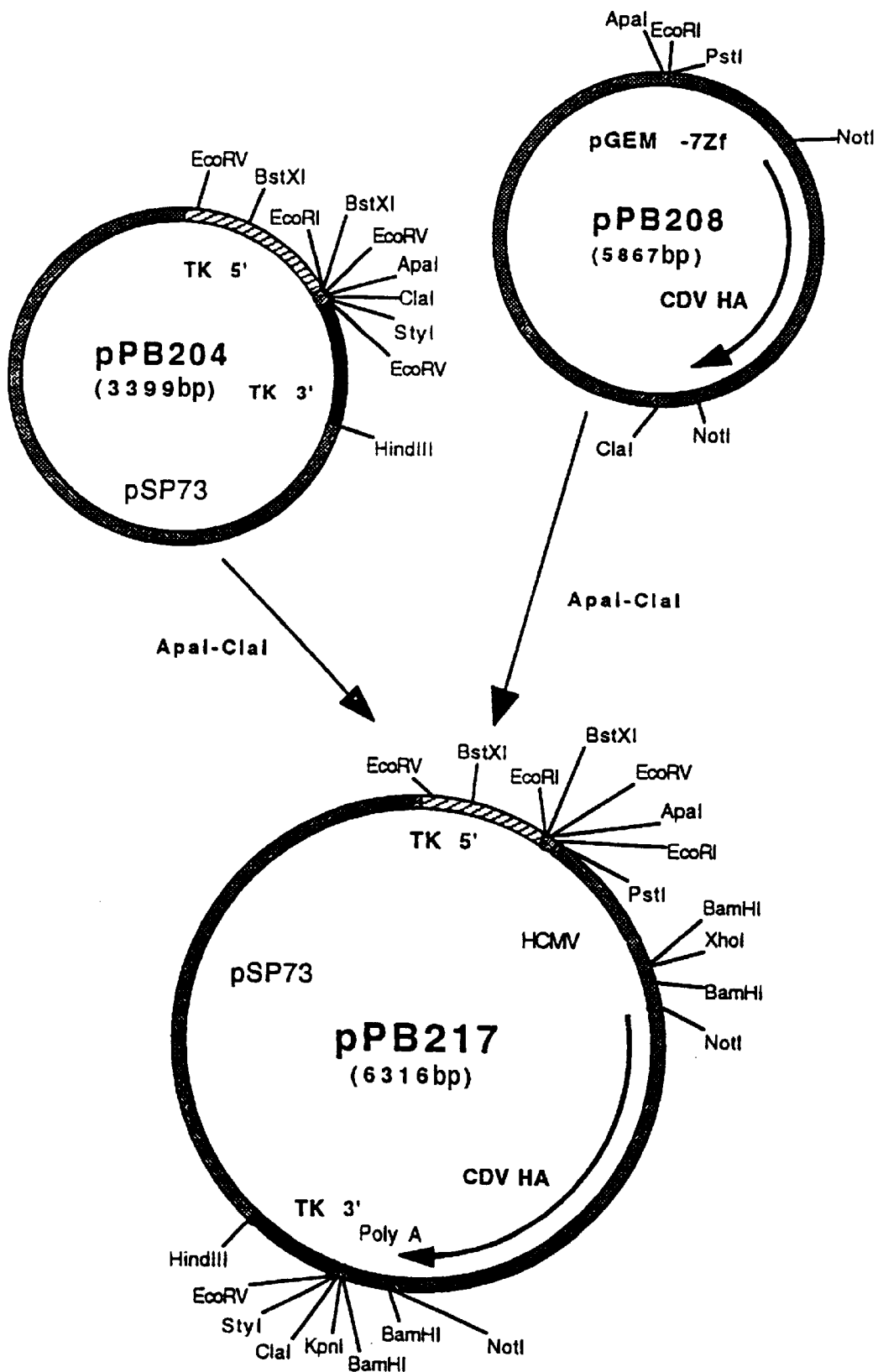

Example 12: Construction of the donor plasmid pPB217 for the insertion of the CDV HA expression cassette into the CHV TK site (FIG. 14)

Plasmid pPB208 (Example 7.1.) was digested with ApaI and ClaI to isolate a 2920-bp fragment containing the cassette for the expression of the CDV HA gene. This fragment was ligated with plasmid pPB204 (Example 5), previously digested with ApaI and ClaI, to give plasmid pPB217 (6316 bp). This plasmid permits the insertion of the cassette for the expression of the CDV HA gene into the CHV TK site.

Figure 15:
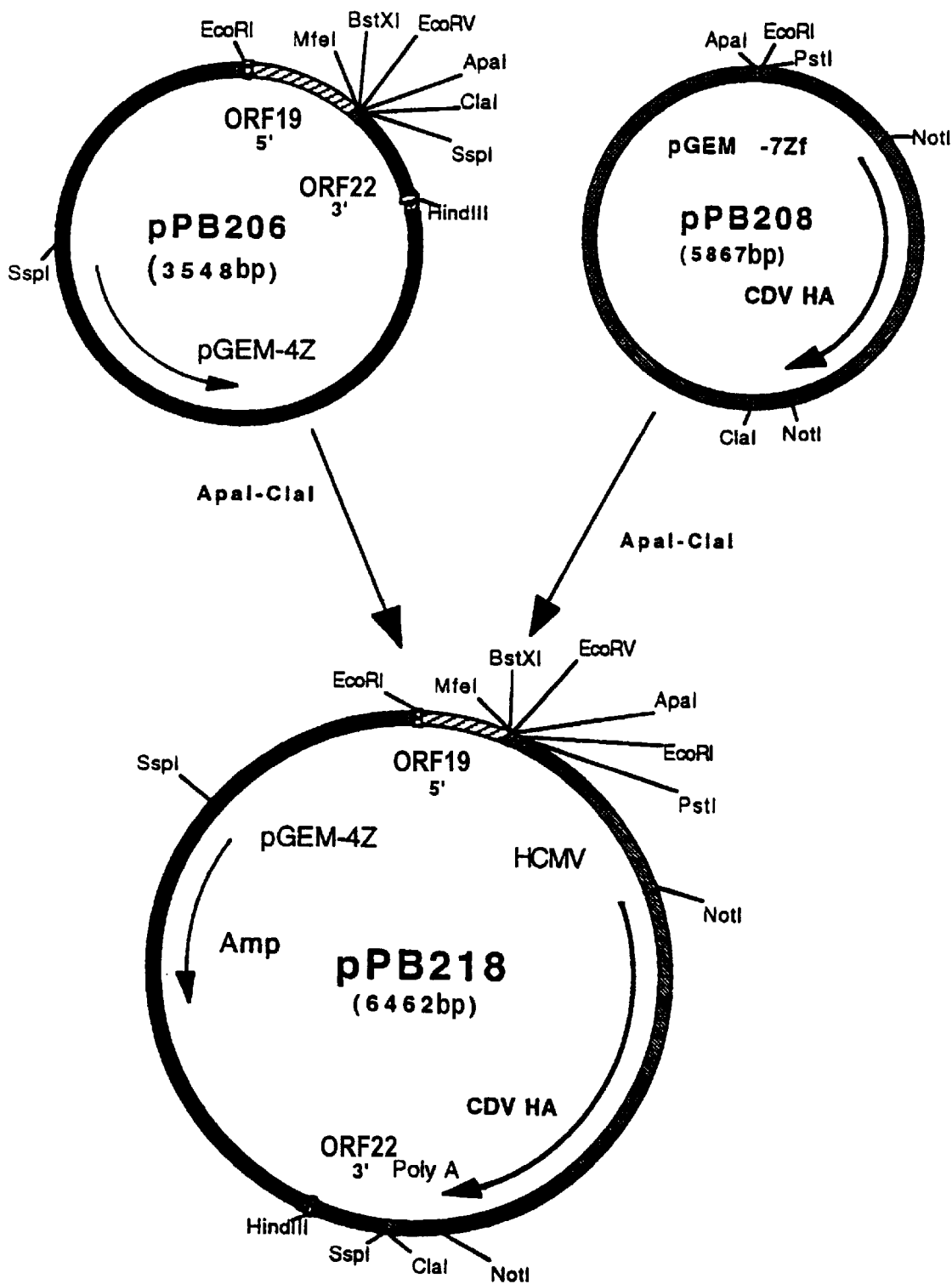

Example 13: Construction of the donor plasmid pPB218 for the insertion of the CDV HA expression cassette into the site situated between the CHV ORF19 and CHV ORF22 genes (FIG. 15)

Plasmid pPB208 (Example 7.1.) was digested with ApaI and ClaI to isolate a 2920-bp fragment containing the cassette for the expression of the CDV HA gene. This fragment was ligated with plasmid pPB206 (Example 6), previously digested with ApaI and ClaI, to give plasmid pPB218 (6462 bp). This plasmid permits the insertion of the cassette for the expression of the CDV HA gene into the site situated between the CHV ORF19 and CHV ORF22 genes.

Example 14: Isolation of the recombinant virus vCHV01 containing the cassette for the expression of the CDV HA gene in the CHV ORF3 site.

Plasmid pPB213 (see Example 8) was linearized by digestion with HindIII, extracted with a phenol-chloroform mixture, precipitated with absolute ethanol and then taken up in sterile water.

MDCK cells forming a well-established cell lawn in a Petri dish (Corning 4.5 cm in diameter) were then transfected with the following mixture:

1 $\mu$g of linearized plasmid pPB213+5 $\mu$g of CHV viral DNA in 300 $\mu$l of MEM medium and 100 $\mu$g of LipofectAMINE (Gibco-BRL Cat#18324-012) diluted in 300 $\mu$l of medium (final volume of the mixture=600 $\mu$l). These 600 $\mu$l were then diluted in 3 ml (final volume) of MEM medium and spread over 3×10$^6$ MDCK cells. The mixture was left in contact with the cells for 5 hours, then removed and replaced by 5 ml of culture medium. The cells were then left in culture for 24 hours at +37° C. After 24 hours to 48 hours of culture, 1 ml of culture supernatant was harvested, and several dilutions of this supernatant were used to infect other MDCK cells (cultured in Petri dishes (Corning 4.5 cm in diameter)) so as to obtain isolated plaques, each dish being infected with 1 ml of a dilution of the initial supernatant. After contact for 1 hour at 37° C., the infection medium was removed and replaced by 5 ml of MEM medium containing 1% of agarose, kept supercooled at 42° C. When the agarose had solidified, the dishes were incubated for 48 hours at 37° C. in a $CO_2$ incubator until plaques were seen. The agarose layer was then removed, and a transfer of the viral plaques was carried out onto a sterile nitrocellulose membrane of the same diameter as the Petri dish used for culturing. This membrane was itself transferred onto another nitrocellulose membrane so as to obtain an inverted "copy" of the first transfer. The plaques transferred onto this second copy were then hybridized, according to the standard techniques known to a person skilled in the art, with a 1842-bp NotI-NotI fragment of the CDV HA gene, obtained by digestion of plasmid pPB208 (Example 7.1.), labelled with digoxigenin (DNA Labelling kit, Boehringer Mannheim, CAT#1175033). After hybridization, washes and contacting with the visualization substrate, the nitrocellulose membrane was placed in contact with an autoradiographic film. The images of positive hybridization on this membrane indicated which plaques were the ones which contained recombinant CHV viruses which had inserted the CDV HA cassette. The plaques corresponding to these positive plaques were cut out under sterile conditions from the first nitrocellulose membrane, placed in an Eppendorf tube containing 0.5 ml of MEM medium and sonicated to release the virions from the membrane. The medium contained in the Eppendorf tube was then diluted in MEM medium, and the dilutions thereby obtained were used to infect further cultures of MDCK cells. A 100% pure recombinant virus containing the HCMV-IE/CDV HA/polyA cassette inserted into the ORF3 site was thereby isolated after 3 cycles of purification, and was called vCHV01. The homology of the recombination was verified by PCR using oligonucleotides situated on each side of the insertion site. The absence of reorganization on the genome of the recombinant virus vCHV01, other than in the recombination region, was verified by the Southern blot technique.

Example 15: Isolation of recombinant CHV viruses expressing various foreign genes According to the procedure described in Example 14, the construction of different recombinant CHV viruses is carried out using the donor plasmids described in Examples 9 to 13.

Example 16: Preparation of the vaccines

To prepare a vaccine, the recombinant viruses obtained in Examples 14 and 15 are cultured on MDCK cells. Harvesting of the recombinant virus takes place when the cytopathic effect is complete. The lysed cells and the culture supernatant are harvested. After clarification of the cell lysate to remove cell debris, the viral solution is titrated. The viral solution is then diluted in a stabilizing solution for lyophilization, distributed on the basis of one vaccinal dose ($10^2$ CCID50 to $10^7$ CCID50) per vial and lastly lyophilized. The viral solution can then be frozen if necessary.

Example 17: Vaccination methods

According to the preferred mode of vaccination, the vaccine obtained according to the invention is redissolved or thawed, and then administered via the parenteral or mucosal route, but preferably via the mucosal, in particular the oral and/or nasal, route. The vaccinal dose will preferably be between $10^2$ CCID50 and $10^7$ CCID50. Preferably, the dose for the parenteral route will be between $10^4$ CCID50 and $10^7$ CCID50, and for the oral and/or nasal route, between $10^2$ CCID50 and $10^5$ CCID50. As defined, the vaccine is effective in general after a single administration via the oral and/or nasal route. However, repeated administrations may be necessary.

What is claimed is:

1. A recombinant canine herpes virus (CHV) comprising and expressing at least one heterologous nucleotide sequence in at least one insertion site comprising ORF3 (SEQ ID NO:5).

2. The recombinant CHV according to claim 1 wherein the at least one heterologous nucleotide sequence encodes an antigen selected from the group consisting of canine distemper virus HA, canine distemper virus F, rabies virus G, canine parvovirus VP2, parainfluenza virus type 2 HA, parainfluenza virus type 2 F, *Borrelia burgdorferi* OspA, and *Borrelia burgdorferi* OspB.

3. The recombinant CHV of claim 1 wherein the at least one heterologous nucleotide sequence is inserted by simple insertion, or after total or partial deletion of the insertion locus.

4. The recombinant CHV according to claim 1 further comprising a strong eukaryotic promoter; wherein at least one heterologous nucleotide sequence is operably linked to the strong eukaryotic promoter.

5. The recombinant CHV according to claim 4 wherein the strong eukaryotic promoter comprises a CMV immediate-early promoter.

6. The recombinant CHV of claim 5 wherein the CMV immediate-early promoter comprises a murine or human CMV immediate-early promoter.

7. The recombinant CHV according to claim 1 comprising at least two heterologous nucleotide sequences inserted into at least one insertion site wherein each heterologous nucleotide sequence is under the control of a different eukaryotic promoter.

8. The recombinant CHV according to claim 7 wherein the eukaryotic promoters are CMV immediate-early promoters of different animal origin.

9. The recombinant CHV according to claim 7 comprising a first heterologous nucleotide sequence operably linked to a first promoter and a second heterologous nucleotide sequence operably linked to a second promoter; wherein, the first promoter comprises a CMV immediate-early promoter, and, the first and second promoters are arranged so that their 5' ends are adjacent.

10. The recombinant CHV according to claim 2 further comprising at least one heterologous nucleotide sequence encoding an immunomodulatory polypeptide.

11. The recombinant CHV according to claim 9 wherein the heterologous nucleotide sequence comprises a nucleotide sequence selected from the group consisting of nucleotide sequences encoding cytokines.

12. The recombinant CHV according to claim 1 wherein the heterologous nucleotide sequence comprises an expression cassette comprising from 5' to 3', a promoter, two or more coding regions separated in pairs by an internal ribosome entry site (IRES), and a polyadenylation signal.

13. The recombinant CHV of claim 2 comprising and expressing at least one heterologous nucleotide sequence encoding the canine distemper virus HA antigen.

14. The recombinant CHV of claim 2 comprising and expressing at least one heterologous nucleotide sequence encoding the canine distemper virus F antigen.

15. The recombinant CHV of claim 2 comprising and expressing at least one heterologous nucleotide sequence encoding the rabies virus G antigen.

16. The recombinant CHV of claim 2 comprising and expressing at least one heterologous nucleotide sequence encoding the canine parvovirus VP2 antigen.

17. The recombinant CHV of claim 2 comprising and expressing at least one heterologous nucleotide sequence encoding the parainfluenza virus type 2 HA antigen.

18. The recombinant CHV of claim 2 comprising and expressing at least one heterologous nucleotide sequence encoding the parainfluenza virus type 2 F antigen.

19. The recombinant CHV of claim 2 comprising and expressing at least one heterologous nucleotide sequence encoding the *Borrelia burgdorferi* OspA antigen.

20. The recombinant CHV of claim 2 comprising and expressing at least one heterologous nucleotide sequence encoding the *Borrelia burgdorferi* OspB antigen.

21. The recombinant CHV according to claim 1 wherein the at least one heterologous nucleotide sequence encodes an antigen.

22. The recombinant CHV according to claim 1 wherein the at least one heterologous nucleotide sequence encodes an immunomodulatory polypeptide.

23. An immunological composition comprising a recombinant CHV as claimed in any one of claims 1 to 20, or 21 or 22.

24. A multivalent immunological composition comprising, as a mixture or to be admixed, at least a first recombinant CHV and a second recombinant CHV; wherein the first and second recombinant CHV are as claimed in any one of claims 1 to 20 or 21 or 22, and the heterologous nucleotide sequence in the first recombinant CHV is different than the heterologous nucleotide sequence in the second recombinant CHV.

25. A method for inducing an immunological response in a canine comprising administering to the canine a recombinant CHV as claimed in any one of claims 1 to 20, or 21 or 22.

26. A method for inducing an immunological response in a canine animal comprising administering to the canine an immunological composition as claimed in claim 23.

27. A method for inducing an immunological response in a canine comprising administering to the canine an immunological composition as claimed in claim 24.

28. The method of claim 25 wherein the administering comprises mucosally administering a dose comprising between $10^2$ and $10^5$ CCID50 of the recombinant CHV.

29. The method of claim 26 wherein the administering comprises mucosally administering a dose comprising between $10^2$ and $10^5$ CCID50 of the recombinant CHV.

30. The method of claim 27 wherein the administering comprises mucosally administering a dose comprising between $10^2$ and $10^5$ CCID50 of the recombinant CHV.

31. A method for expressing a polypeptide comprising contacting a suitable cell with a recombinant CHV as claimed in any one of claims 1 to 20 or 21 or 22.

\* \* \* \* \*

UNITED STATES PATENT AND TRADEMARK OFFICE
CERTIFICATE OF CORRECTION

PATENT NO. : 6,159,477
APPLICATION NO. : 09/213053
DATED : December 12, 2000
INVENTOR(S) : Jean-Christophe Audonnet and Philippe Baudu It is certified that error appears in the above-identified patent and that said Letters Patent is hereby corrected as shown below:

IN THE CLAIMS:

Column 41, line 63 claim 1: delete "5" and insert therefor --4--.

Signed and Sealed this

Fifteenth Day of January, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,159,477 | Page 1 of 1 |
| APPLICATION NO. | : 09/213053 | |
| DATED | : December 12, 2000 | |
| INVENTOR(S) | : Jean-Christophe Audonnet and Philippe Baudu | |

It is certified that error appears in the above-identified patent and that said Letters Patent is hereby corrected as shown below:

<u>IN THE CLAIMS</u>:

Column 41, line 63 delete "4" and insert therefor -- 5 --.

Signed and Sealed this

Eleventh Day of November, 2008

JON W. DUDAS
*Director of the United States Patent and Trademark Office*

SEQUENCE LISTING

```
<160> NUMBER OF SEQ ID NOS: 31

<210> SEQ ID NO 1
<211> LENGTH: 6216
<212> TYPE: DNA
<213> ORGANISM: Canine herpesvirus

<400> SEQUENCE: 1
```

-continued

```
ctcgaggaaa ttgtttgttt gtatctacaa aacttcaaaa tatctttgtt tattgtctct      60
tcgatggatt ttattttcat cttcgcgatt gattcttcct tggttaccgt aatttataaa     120
taaacacaat aaaaattaag tttaaaaaca attttattaa acccatcgtc ttgatttact     180
atcatcccag taggaaatta gaactagatt ataatctatc ggtatagaaa tatgtttcca     240
aaataaatta gttaaatttt tagccttttc tttatcatct ataaagctta aaagtgtttc     300
ataaacaaga tttatatcaa acttttcttg gataattgga actcttttaa ttatagataa     360
attttcaccc ctatattctg gggttatcat atttgttaga tgtttaataa attttctctc     420
caacacttcg tgtttggttt ggggtgccgg aagcatcatt aaagaacggg atatcgtttt     480
cattattggt ggaaatcttg atgtatattt taaatttaaa ctattctcat caacagctgt     540
tacgcgcttt gattgtcctt tatttgatgg agagtttatt tttgataaaa ttttaaatcc     600
attttgattt tttggtatac caaatgaatc ggtatcacta ctttcactac tggtaatatt     660
tgaggattct tcggatgatg aaactatatt tgtagaaaca gaatcactta ttctccatga     720
gtttgatatt tgatctaaat attttttcatg atgttgtatt tctcctgatt cttcagatga     780
atctccacta tcagaattat attccttttt actattttta tatttatttt taataattga     840
ttgaacagat tttaaaatag gggcttggtg caagtctgta tgacagcgaa caaacgtaca     900
taaaaactca ggatatgata catttaaaga agcaagtata tccctacatc ggagggtggg     960
tggaaaaaga ggtacaacat ccaatataat atcacaaccc attaatatta gatcagtatc    1020
cgttgtatat atttgagcgg ctgtattagt atgataaaga ttagcacaaa catcatcagc    1080
ttccatatca gatacattaa catatggaaa acccaaatgg cgtattaaat taacacataa    1140
tttataacat aacttaggag tatttacaag tgagctccat cgtgctgata aaatatttat    1200
aggttcacat ttttccaatt ttttgtaagt tttttaaaatt tccccacata cattatcctt    1260
aatggaattt ctccaagtct tccagatcct ccttgatgac acatagtttg tgtggcgata    1320
cgtttgctcc acgtttaaca tgtccatcac catttatacc acgatctgaa acaaaaattg    1380
gaaaataaga tcttttttgg agtaatttaa gtaaagaaaa aaaacattca gctgttacag    1440
tgggactatc cgtttgagta tcattttcta tacaaaattt ttccatcaac gtatacatta    1500
cattccataa gtcaattgcg attggtgtac aataccaggt ggtgttgcta tcgcatcgtg    1560
tttaactagt ctacgactat aagcatattt caaaagtcca aaaagaccca ttttaataaa    1620
ataccaaaca gaaccttttc gacaaactaa atgaataaaa ctagtttttta agtattaaat    1680 ataacctttta actaaattaa ttaaataatg attaatttaa aaaccgaaat acaaatattt    1740
tttagtcaag attttatgaa atcaatcaaa atcaccacaa ttatgcaaat gaacccacct    1800
accaacgtca tcaaaactaa tttagtctat aaaaagaaat tgttaacatt tagtttaaat    1860
ttaaactttt atttcttaaa attttttatta ttttgcttag ttttaaggc gatggcgtgt    1920 tttcgtccta aaactgaatt taagataacc aaccatccat ctcagattat aaataacgaa    1980
gaaaatataa actctgaaga aggaaatttt atatctggtc gtgctgtttt ggaagatcaa    2040
aagcttcgtg atgtgataag tatgctaaca ccctttccaa ctagcttgaa aaactctttt    2100 atagtttttta gtgactatgg gatgatgatc catactagta tttgtggaga acaaatttac    2160
attcctattt ctaaaaacca attttcttct tattttgggg gatatagcga ccctgcggta    2220
tttttggcaa atgttgatag taaaagggga ttgttggatg ttttaaatc aacaagtaaa    2280 atgtctaaag tattctttga aataagtaac ccttcccaac atagaatgtt aaaacaagtt    2340
```

-continued

```
attttttacta taagtgatag taatatataaaa tgctctacac ttctaaaagc tgaatttagt    2400
aactattgta ttatgcttcc atcaagaaat ccggacttta gtcttgaact taataaatat     2460
caattaaata aaatactcga actaaacaaa aaacaaaatt cattgttaaa atttgaatct     2520
aatgaaaata atgttgtgat ttcatctgaa agtggaagtg tttcattgaa tttggataga    2580
agcgattctg aaggagaaga tagcgcatcg atttttaaaat ctgctacaaa aaaagtaaat    2640
ccttatctag ttaaacactc agaaaatttc aaacgtttaa aatttcgttg gatgattata    2700
ccaatttttt ttcctctttt gaaaaaacta aaactaacaa atacaacagt atcgataaat    2760 ttcttttta ctccaactac caatcccatg ataagcttga cgtcaagtaa accaattgga    2820
attatactgt ttttcttttg taccaatgaa ttgcaacata agagcctgaa gcgcccagca   2880
tctccatcag atgaagaaaa gccaccaaaa atccaatgtg gatttttag tcaacatttt    2940 gtaaatacgg atgttaatat taaaccctaa ttaaatgacg taaaatgata aattgtattt    3000
aaagagaagt tttttccaaa agacaagctt ttattaataa tgtcactaga agataataat    3060
gtacaatcgt tgatcaact ggaacctcct attacatcat tttctataat aaattgctct    3120
ggatcgagac ctggatgtct accatgtatg tatgtaacta caaaatcact tctatgtatt    3180
ggacttcaag ctggaatttt aacagcctta attatattaa ttcaaatatt aactgaaagt    3240
ttcgtatgtt ctataattct tatagcaact gtgttaatat ttacgctatc aaaaatatct    3300
atttctactt ctgaaaaaat ttcttctatt tgtagaatta gtcagtcgat atttgtaaca    3360
atagccgcct tttgttgggg gtttgattgg atattaaatc caatagcaat taaaataatt    3420
cttatattaa gtttatcatt tttaactatt tgtacaataa aaatacatat attttatttg    3480
ataagtatat taaatggttc tggatctcat gtaaaaggat cgctagtaac aatattgttt    3540
ggaactatac taggtgtatt tggaactctt aatgttatta aaatagaaat tttaattgga    3600
tttggtatag cactttgtat aattttatct aacaccaact ttggactagt aattagagat    3660
acatgctatt atcgtatagg aagatataaa ttaatgagaa cttttacaga tcttggacat    3720
ggagcgtctt actcaataga ggaagatgaa acctctgatt acagtgaaat acatgaaaga    3780
aaaattagta gttttcaact aatttataaa tatccaagta tgataataat ttctatttta    3840
ggatttatgt taactatagc tatttgggga ttaaatgtat acttaaaaaa tttaaaattt    3900
cattctcctt ttacacttgt tattagcttt attgttggtc attgtttagc attcttagtt    3960
gaaccgttta actataagat taaatgtata tcacgaatta tactaattat ttgtcttttta   4020 ctagaattaa ttgcttcact tatttctgta ctaggattaa attttggatc accattaatc   4080
ttgacaacaa ctactacaat ttcgttagtt tcactttttgt atatacgaaa acaaacacaa   4140
ggtgtaaacc gtcttgctgc cacatatatt tcacgagccc taattattgg tttgtatatg   4200
actgttggaa tttgttacat ttttattaaa acaataaatt aaattttta aactatatta   4260 cggttgtgtg tgttttaagt tttaaataaa gcaatatttc gaattcacat ttatcaaaaa   4320
cattaaaacc caacacaaaa aaatttctat aatcattaag gtaataagtc aaaatgagtt   4380
ttaaaaattt ttatctaata tatgtaatta taattttttat aaactcgata ataacttcgg   4440
catctacatc caaaccttca acacctacca taattccaac ttcagcaaat gaatcacctg   4500
cttccataga tacaactata acaaaaccta tatctacaga ggcaaataat ttaaaatcag   4560
taagtacctc aattaaacca cctaaaaact taaaaaaaaa attacttaaa tctaaatgta   4620
gagataatgt tatttatagg ccatatttta gtcaattaga aattaactgt actataacta   4680
aaaagcaaaa tttaagtaat cctttaattg agttatggtt taaagaactt tctacatata   4740
```

-continued

```
ataaaaccaa tgaaatgtt gaaagtttaa aaacagatat atcaaaaaat attttattat    4800
tttcgacaaa aataatagt gataactttt ataatgattt tttattaggt atacaaaatc    4860
aaccagtaaa ttataaactt tacggttccc aattttatga taatgaaac atattactaa    4920 atataaagtc ggttgacttt aaaacctctg gaatatatac ttggaaacta tataattcaa    4980
ataatgaaag tattttttgaa actttttaaaa ttcaagtata tgcatatcat tcaccaaatg   5040
taaacttaaa atcaaaccca agtttatata atgaaaacta cagcgctatt tgtacaatag    5100
caaattactt tccattggaa tctacggaaa tattttggtt taacgatgga caacctattg    5160
ataaaaaata tatagatgaa acttatagtg tatggattga cggtcttata acacgcactt   5220
caatattatc ccttcccttt tccgaagcca tggaaagccc ccccaatttg cgatgtaatg    5280
ttgaatggta taaaaattca aaggcctcaa aaaaattttc aaataccgtt attccaaaag    5340
tttactataa acctttttata tctataaaat ttgataatgg tttagctatt tgtgatgcta   5400
aatgtgtttc ccgtgaaaat aataaattac aatggttagt taaagatata cctataaatg   5460
gtgatgatat tataagcggc ccctgtttaa accaccctgg tttggtcaat attcaaaata   5520
aaatagatat atcggattat gatgaacctg ttacctataa atgttcaatt attggttatc   5580
caataatttt tcccaactt tatgatgaaa aggtgtttga tgcatcggat gaaaatgtta   5640
gtaaatcgat gttaataagt attaccacaa taattggtgg agccattttt gttatagtat    5700 tgattttat aacagcttta tgtttttatt gttcaaaaaa taataagatc taatatcaat    5760
atttacgtaa atggattata taatgttata ttcgtgttat tatgatttat aagttcatca   5820
aatttaaaaa tttgtatagt attaagattt ttaatagggg tatcgtttaa tatggctcag   5880
ttagttttaa ctgatattcc cctcgaagat gtggaaaata aaatacttc atccgacgaa    5940 gaaacaacta acttaaacca gaaaaaatca acatgtcaat gtttatgtgt tacccttgga   6000
ttttttgcag ctggaattt attaaccata gctgcaataa ttttttacttt tatttttaca   6060 gtaccattag aaatgcttgg atcgattaat tgtcctccat ctacatttgg tattgataat    6120
gtttgtatcg aaccaataaa aaaatctatt aattcttatt cagaattatc taaaatatgt    6180
tatgatagat tgtcaaatcc gataaatcag agtact    6216
```

<210> SEQ ID NO 2
<211> LENGTH: 1394
<212> TYPE: PRT
<213> ORGANISM: Canine herpesvirus

<400> SEQUENCE: 2

```
Met Ile Asn Leu Lys Thr Glu Ile Gln Ile Phe Phe Ser Gln Asp Phe
  1               5                  10                  15

Met Lys Ser Ile Lys Ile Thr Thr Ile Met Gln Met Asn Pro Pro Thr
             20                  25                  30

Asn Val Ile Lys Thr Asn Leu Val Tyr Lys Lys Leu Leu Thr Phe
         35                  40                  45

Ser Leu Asn Leu Asn Phe Tyr Phe Leu Lys Phe Leu Phe Cys Leu
     50                  55                  60

Val Phe Lys Ala Met Ala Cys Phe Arg Pro Lys Thr Glu Phe Lys Ile
 65                  70                  75                  80

Thr Asn His Pro Ser Gln Ile Ile Asn Glu Glu Asn Ile Asn Ser
                 85                  90                  95

Glu Glu Gly Lys Phe Ile Ser Gly Arg Ala Val Leu Glu Asp Gln Lys
            100                 105                 110
```

-continued

```
Leu Arg Asp Val Ile Ser Met Leu Thr Pro Phe Ser Thr Ser Leu Lys
        115                 120                 125

Asn Ser Phe Ile Val Phe Ser Asp Tyr Gly Met Met Ile His Thr Ser
        130                 135                 140

Ile Cys Gly Glu Gln Ile Tyr Ile Pro Ile Ser Lys Asn Gln Phe Ser
145                 150                 155                 160

Ser Tyr Phe Trp Gly Tyr Ser Asp Pro Ala Val Phe Leu Ala Asn Val
                165                 170                 175

Asp Ser Lys Arg Gly Leu Leu Asp Val Phe Lys Ser Thr Ser Lys Met
            180                 185                 190

Ser Lys Val Phe Phe Glu Ile Ser Asn Pro Ser Gln His Arg Met Leu
        195                 200                 205

Lys Gln Val Ile Phe Thr Ile Ser Asp Ser Asn Ile Lys Cys Ser Thr
        210                 215                 220

Leu Leu Lys Ala Glu Phe Ser Asn Tyr Cys Ile Met Leu Pro Ser Arg
225                 230                 235                 240

Asn Pro Asp Phe Ser Leu Glu Leu Asn Lys Tyr Gln Leu Asn Lys Ile
                245                 250                 255

Leu Glu Leu Asn Lys Lys Gln Asn Ser Leu Leu Lys Phe Glu Ser Asn
            260                 265                 270

Glu Asn Asn Val Val Ile Ser Ser Glu Ser Gly Ser Val Ser Leu Asn
        275                 280                 285

Leu Asp Arg Ser Asp Ser Glu Gly Glu Asp Ser Ala Ser Ile Leu Lys
        290                 295                 300

Ser Ala Thr Lys Lys Val Asn Pro Tyr Leu Val Lys His Ser Glu Asn
305                 310                 315                 320

Phe Lys Arg Leu Lys Phe Arg Trp Met Ile Ile Pro Ile Phe Phe Pro
                325                 330                 335

Leu Leu Lys Lys Leu Lys Leu Thr Asn Thr Thr Val Ser Ile Asn Phe
            340                 345                 350

Phe Phe Thr Pro Thr Thr Asn Pro Met Ile Ser Leu Thr Ser Ser Lys
        355                 360                 365

Pro Ile Gly Ile Ile Leu Phe Phe Phe Cys Thr Asn Glu Leu Gln His
370                 375                 380

Lys Ser Leu Lys Arg Pro Ala Ser Pro Ser Asp Glu Glu Lys Pro Pro
385                 390                 395                 400

Lys Ile Gln Cys Gly Phe Phe Ser Gln His Phe Val Asn Thr Asp Val
                405                 410                 415

Asn Ile Lys Pro Met Ser Leu Glu Asp Asn Asn Val Gln Ser Phe Asp
            420                 425                 430

Gln Leu Glu Pro Pro Ile Thr Ser Phe Ser Ile Ile Asn Cys Ser Gly
        435                 440                 445

Ser Arg Pro Gly Cys Leu Pro Cys Met Tyr Val Thr Thr Lys Ser Leu
        450                 455                 460

Leu Cys Ile Gly Leu Gln Ala Gly Ile Leu Thr Ala Leu Ile Ile Leu
465                 470                 475                 480

Ile Gln Ile Leu Thr Glu Ser Phe Val Cys Ser Ile Ile Leu Ile Ala
                485                 490                 495

Thr Val Leu Ile Phe Thr Leu Ser Lys Ile Ser Ile Ser Thr Ser Glu
            500                 505                 510

Lys Ile Ser Ser Ile Cys Arg Ile Ser Gln Ser Ile Phe Val Thr Ile
        515                 520                 525
```

```
Ala Ala Phe Cys Trp Gly Phe Asp Trp Ile Leu Asn Pro Ile Ala Ile
        530                 535                 540

Lys Ile Ile Leu Ile Leu Ser Leu Ser Phe Leu Thr Ile Cys Thr Ile
545                 550                 555                 560

Lys Ile His Ile Phe Tyr Leu Ile Ser Ile Leu Asn Gly Ser Gly Ser
                    565                 570                 575

His Val Lys Gly Ser Leu Val Thr Ile Leu Phe Gly Thr Ile Leu Gly
            580                 585                 590

Val Phe Gly Thr Leu Asn Val Ile Lys Ile Glu Ile Leu Ile Gly Phe
        595                 600                 605

Gly Ile Ala Leu Cys Ile Ile Leu Ser Asn Thr Asn Phe Gly Leu Val
    610                 615                 620

Ile Arg Asp Thr Cys Tyr Tyr Arg Ile Gly Tyr Lys Leu Met Arg
625                 630                 635                 640

Thr Phe Thr Asp Leu Gly His Gly Ala Ser Tyr Ser Ile Glu Glu Asp
                    645                 650                 655

Glu Thr Ser Asp Tyr Ser Glu Ile His Glu Arg Lys Ile Ser Ser Phe
            660                 665                 670

Gln Leu Ile Tyr Lys Tyr Pro Ser Met Ile Ile Ser Ile Leu Gly
        675                 680                 685

Phe Met Leu Thr Ile Ala Ile Trp Gly Leu Asn Val Tyr Leu Lys Asn
    690                 695                 700

Leu Lys Phe His Ser Pro Phe Thr Leu Val Ile Ser Phe Ile Val Gly
705                 710                 715                 720

His Cys Leu Ala Phe Leu Val Glu Pro Phe Asn Tyr Lys Ile Lys Cys
                    725                 730                 735

Ile Ser Arg Ile Ile Leu Ile Ile Cys Leu Leu Leu Glu Leu Ile Ala
            740                 745                 750

Ser Leu Ile Ser Val Leu Gly Leu Asn Phe Gly Ser Pro Leu Ile Leu
        755                 760                 765

Thr Thr Thr Thr Thr Ile Ser Leu Val Ser Leu Leu Tyr Ile Arg Lys
    770                 775                 780

Gln Thr Gln Gly Val Asn Arg Leu Ala Ala Thr Tyr Ile Ser Arg Ala
785                 790                 795                 800

Leu Ile Ile Gly Leu Tyr Met Thr Val Gly Ile Cys Tyr Ile Phe Ile
                    805                 810                 815

Lys Thr Ile Asn Met Ser Phe Lys Asn Phe Tyr Leu Ile Tyr Val Ile
            820                 825                 830

Ile Ile Phe Ile Asn Ser Ile Ile Thr Ser Ala Ser Thr Ser Lys Pro
        835                 840                 845

Ser Thr Pro Thr Ile Ile Pro Thr Ser Ala Asn Glu Ser Pro Ala Ser
    850                 855                 860

Ile Asp Thr Thr Ile Thr Lys Pro Ile Ser Thr Glu Ala Asn Asn Leu
865                 870                 875                 880

Lys Ser Val Ser Thr Ser Ile Lys Pro Pro Lys Asn Leu Lys Lys Lys
                    885                 890                 895

Leu Leu Lys Ser Lys Cys Arg Asp Asn Val Ile Tyr Arg Pro Tyr Phe
            900                 905                 910

Ser Gln Leu Glu Ile Asn Cys Thr Ile Thr Lys Lys Gln Asn Leu Ser
        915                 920                 925

Asn Pro Leu Ile Glu Leu Trp Phe Lys Glu Leu Ser Thr Tyr Asn Lys
    930                 935                 940

Thr Asn Glu Asn Val Glu Ser Leu Lys Thr Asp Ile Ser Lys Asn Ile
```

-continued

```
945                 950                 955                 960
Leu Leu Phe Ser Thr Lys Asn Asn Ser Asp Asn Phe Tyr Asn Asp Phe
                965                 970                 975
Leu Leu Gly Ile Gln Asn Gln Pro Val Asn Tyr Lys Leu Tyr Gly Ser
                980                 985                 990
Gln Phe Tyr Asp Asn Gly Asn Ile Leu Leu Asn Ile Lys Ser Val Asp
                995                 1000                1005
Phe Lys Thr Ser Gly Ile Tyr Thr Trp Lys Leu Tyr Asn Ser Asn Asn
    1010                1015                1020
Glu Ser Ile Phe Glu Thr Phe Lys Ile Gln Val Tyr Ala Tyr His Ser
1025                1030                1035                1040
Pro Asn Val Asn Leu Lys Ser Asn Pro Ser Leu Tyr Asn Glu Asn Tyr
                1045                1050                1055
Ser Ala Ile Cys Thr Ile Ala Asn Tyr Phe Pro Leu Glu Ser Thr Glu
                1060                1065                1070
Ile Phe Trp Phe Asn Asp Gly Gln Pro Ile Asp Lys Lys Tyr Ile Asp
                1075                1080                1085
Glu Thr Tyr Ser Val Trp Ile Asp Gly Leu Ile Thr Arg Thr Ser Ile
    1090                1095                1100
Leu Ser Leu Pro Phe Ser Glu Ala Met Glu Ser Pro Pro Asn Leu Arg
1105                1110                1115                1120
Cys Asn Val Glu Trp Tyr Lys Asn Ser Lys Ala Ser Lys Lys Phe Ser
                1125                1130                1135
Asn Thr Val Ile Pro Lys Val Tyr Tyr Lys Pro Phe Ile Ser Ile Lys
                1140                1145                1150
Phe Asp Asn Gly Leu Ala Ile Cys Asp Ala Lys Cys Val Ser Arg Glu
    1155                1160                1165
Asn Asn Lys Leu Gln Trp Leu Val Lys Asp Ile Pro Ile Asn Gly Asp
    1170                1175                1180
Asp Ile Ile Ser Gly Pro Cys Leu Asn His Pro Gly Leu Val Asn Ile
1185                1190                1195                1200
Gln Asn Lys Ile Asp Ile Ser Asp Tyr Asp Glu Pro Val Thr Tyr Lys
                1205                1210                1215
Cys Ser Ile Ile Gly Tyr Pro Ile Ile Phe Pro Asn Phe Tyr Asp Glu
                1220                1225                1230
Lys Val Phe Asp Ala Ser Asp Glu Asn Val Ser Lys Ser Met Leu Ile
                1235                1240                1245
Ser Ile Thr Thr Ile Ile Gly Gly Ala Ile Phe Val Ile Val Leu Ile
    1250                1255                1260
Phe Ile Thr Ala Leu Cys Phe Tyr Cys Ser Lys Asn Asn Lys Ile Met
1265                1270                1275                1280
Ala Gln Leu Val Leu Thr Asp Ile Pro Leu Glu Asp Val Glu Asn Lys
                1285                1290                1295
Asn Thr Ser Ser Asp Glu Glu Thr Thr Asn Leu Asn Gln Lys Lys Ser
                1300                1305                1310
Thr Cys Gln Cys Leu Cys Val Thr Leu Gly Phe Phe Ala Ala Gly Ile
    1315                1320                1325
Leu Leu Thr Ile Ala Ala Ile Ile Phe Thr Phe Ile Phe Thr Val Pro
    1330                1335                1340
Leu Glu Met Leu Gly Ser Ile Asn Cys Pro Pro Ser Thr Phe Gly Ile
1345                1350                1355                1360
Asp Asn Val Cys Ile Glu Pro Ile Lys Lys Ser Ile Asn Ser Tyr Ser
                1365                1370                1375
```

Glu Leu Ser Lys Ile Cys Tyr Asp Arg Leu Ser Asn Pro Ile Asn Gln
             1380                1385                1390

Ser Thr

<210> SEQ ID NO 3
<211> LENGTH: 398
<212> TYPE: PRT
<213> ORGANISM: Canine herpesvirus

<400> SEQUENCE: 3

Met Val Met Asp Met Leu Asn Val Glu Gln Thr Tyr Arg His Thr Asn
 1               5                  10                  15

Tyr Val Ser Ser Arg Arg Ile Trp Lys Thr Trp Arg Asn Ser Ile Lys
            20                  25                  30

Asp Asn Val Cys Gly Glu Ile Leu Lys Thr Tyr Lys Lys Leu Glu Lys
            35                  40                  45

Cys Glu Pro Ile Asn Ile Leu Ser Ala Arg Trp Ser Ser Leu Val Asn
    50                  55                  60

Thr Pro Lys Leu Cys Tyr Lys Leu Cys Val Asn Leu Ile Arg His Leu
 65                  70                  75                  80

Gly Phe Pro Tyr Val Asn Val Ser Asp Met Glu Ala Asp Asp Val Cys
                85                  90                  95

Ala Asn Leu Tyr His Thr Asn Thr Ala Ala Gln Ile Tyr Thr Thr Asp
            100                 105                 110

Thr Asp Leu Ile Leu Met Gly Cys Asp Ile Ile Leu Asp Val Val Pro
        115                 120                 125

Leu Phe Pro Pro Thr Leu Arg Cys Arg Asp Ile Leu Ala Ser Leu Asn
130                 135                 140

Val Ser Tyr Pro Glu Phe Leu Cys Thr Phe Val Arg Cys His Thr Asp
145                 150                 155                 160

Leu His Gln Ala Pro Ile Leu Lys Ser Val Gln Ser Ile Ile Lys Asn
                165                 170                 175

Lys Tyr Lys Asn Ser Lys Lys Glu Tyr Asn Ser Asp Ser Gly Asp Ser
            180                 185                 190

Ser Glu Glu Ser Gly Glu Ile Gln His His Glu Lys Tyr Leu Asp Gln
        195                 200                 205

Ile Ser Asn Ser Trp Arg Ile Ser Asp Ser Val Ser Thr Asn Ile Val
    210                 215                 220

Ser Ser Glu Glu Ser Ser Asn Ile Thr Ser Glu Ser Ser Asp
225                 230                 235                 240

Thr Asp Ser Phe Gly Ile Pro Lys Asn Gln Asn Gly Phe Lys Ile Leu
                245                 250                 255

Ser Lys Ile Asn Ser Pro Ser Asn Lys Gly Gln Ser Lys Arg Val Thr
            260                 265                 270

Ala Val Asp Glu Asn Ser Leu Asn Leu Lys Tyr Thr Ser Arg Phe Pro
        275                 280                 285

Pro Ile Met Lys Thr Ile Ser Arg Ser Leu Met Met Leu Pro Ala Pro
    290                 295                 300

Gln Thr Lys His Glu Val Leu Glu Arg Lys Phe Ile Lys His Leu Thr
305                 310                 315                 320

Asn Met Ile Thr Pro Glu Tyr Arg Gly Glu Asn Leu Ser Ile Ile Lys
                325                 330                 335

Arg Val Pro Ile Ile Gln Glu Lys Phe Asp Ile Asn Leu Val Tyr Glu
            340                 345                 350

-continued

```
Thr Leu Leu Ser Phe Ile Asp Asp Lys Glu Lys Ala Lys Asn Leu Thr
            355                 360                 365

Asn Leu Phe Trp Lys His Ile Ser Ile Pro Ile Asp Tyr Asn Leu Val
            370                 375                 380

Leu Ile Ser Tyr Trp Asp Asp Ser Lys Ser Arg Arg Trp Val
385                 390                 395

<210> SEQ ID NO 4
<211> LENGTH: 420
<212> TYPE: PRT
<213> ORGANISM: Canine herpesvirus

<400> SEQUENCE: 4

Met Ile Asn Leu Lys Thr Glu Ile Gln Ile Phe Phe Ser Gln Asp Phe
1               5                   10                  15

Met Lys Ser Ile Lys Ile Thr Thr Ile Met Gln Met Asn Pro Pro Thr
            20                  25                  30

Asn Val Ile Lys Thr Asn Leu Val Tyr Lys Lys Leu Leu Thr Phe
            35                  40                  45

Ser Leu Asn Leu Asn Phe Tyr Phe Leu Lys Phe Leu Leu Phe Cys Leu
        50                  55                  60

Val Phe Lys Ala Met Ala Cys Phe Arg Pro Lys Thr Glu Phe Lys Ile
65                  70                  75                  80

Thr Asn His Pro Ser Gln Ile Ile Asn Asn Glu Glu Asn Ile Asn Ser
                85                  90                  95

Glu Glu Gly Lys Phe Ile Ser Gly Arg Ala Val Leu Glu Asp Gln Lys
            100                 105                 110

Leu Arg Asp Val Ile Ser Met Leu Thr Pro Phe Ser Thr Ser Leu Lys
            115                 120                 125

Asn Ser Phe Ile Val Phe Ser Asp Tyr Gly Met Met Ile His Thr Ser
        130                 135                 140

Ile Cys Gly Glu Gln Ile Tyr Ile Pro Ile Ser Lys Asn Gln Phe Ser
145                 150                 155                 160

Ser Tyr Phe Trp Gly Tyr Ser Asp Pro Ala Val Phe Leu Ala Asn Val
                165                 170                 175

Asp Ser Lys Arg Gly Leu Leu Asp Val Phe Lys Ser Thr Ser Lys Met
            180                 185                 190

Ser Lys Val Phe Phe Glu Ile Ser Asn Pro Ser Gln His Arg Met Leu
            195                 200                 205

Lys Gln Val Ile Phe Thr Ile Ser Asp Ser Asn Ile Lys Cys Ser Thr
        210                 215                 220

Leu Leu Lys Ala Glu Phe Ser Asn Tyr Cys Ile Met Leu Pro Ser Arg
225                 230                 235                 240

Asn Pro Asp Phe Ser Leu Glu Leu Asn Lys Tyr Gln Leu Asn Lys Ile
                245                 250                 255

Leu Glu Leu Asn Lys Lys Gln Asn Ser Leu Leu Lys Phe Glu Ser Asn
            260                 265                 270

Glu Asn Asn Val Val Ile Ser Ser Glu Ser Gly Ser Val Ser Leu Asn
            275                 280                 285

Leu Asp Arg Ser Asp Ser Glu Gly Glu Asp Ser Ala Ser Ile Leu Lys
        290                 295                 300

Ser Ala Thr Lys Lys Val Asn Pro Tyr Leu Val Lys His Ser Glu Asn
305                 310                 315                 320

Phe Lys Arg Leu Lys Phe Arg Trp Met Ile Ile Pro Ile Phe Phe Pro
```

```
                    325                 330                 335
Leu Leu Lys Lys Leu Lys Leu Thr Asn Thr Thr Val Ser Ile Asn Phe
                340                 345                 350

Phe Phe Thr Pro Thr Thr Asn Pro Met Ile Ser Leu Thr Ser Ser Lys
            355                 360                 365

Pro Ile Gly Ile Ile Leu Phe Phe Cys Thr Asn Glu Leu Gln His
        370                 375                 380

Lys Ser Leu Lys Arg Pro Ala Ser Pro Ser Asp Glu Lys Pro Pro
385                 390                 395                 400

Lys Ile Gln Cys Gly Phe Phe Ser Gln His Phe Val Asn Thr Asp Val
                405                 410                 415

Asn Ile Lys Pro
            420

<210> SEQ ID NO 5
<211> LENGTH: 400
<212> TYPE: PRT
<213> ORGANISM: Canine herpesvirus

<400> SEQUENCE: 5

Met Ser Leu Glu Asp Asn Asn Val Gln Ser Phe Asp Gln Leu Glu Pro
1               5                   10                  15

Pro Ile Thr Ser Phe Ser Ile Ile Asn Cys Ser Gly Ser Arg Pro Gly
            20                  25                  30

Cys Leu Pro Cys Met Tyr Val Thr Lys Ser Leu Leu Cys Ile Gly
        35                  40                  45

Leu Gln Ala Gly Ile Leu Thr Ala Leu Ile Ile Leu Ile Gln Ile Leu
    50                  55                  60

Thr Glu Ser Phe Val Cys Ser Ile Ile Leu Ile Ala Thr Val Leu Ile
65                  70                  75                  80

Phe Thr Leu Ser Lys Ile Ser Ile Ser Thr Ser Glu Lys Ile Ser Ser
                85                  90                  95

Ile Cys Arg Ile Ser Gln Ser Ile Phe Val Thr Ile Ala Ala Phe Cys
            100                 105                 110

Trp Gly Phe Asp Trp Ile Leu Asn Pro Ile Ala Ile Lys Ile Ile Leu
        115                 120                 125

Ile Leu Ser Leu Ser Phe Leu Thr Ile Cys Thr Ile Lys Ile His Ile
130                 135                 140

Phe Tyr Leu Ile Ser Ile Leu Asn Gly Ser Gly Ser His Val Lys Gly
145                 150                 155                 160

Ser Leu Val Thr Ile Leu Phe Gly Thr Ile Leu Gly Val Phe Gly Thr
                165                 170                 175

Leu Asn Val Ile Lys Ile Glu Ile Leu Ile Gly Phe Gly Ile Ala Leu
            180                 185                 190

Cys Ile Ile Leu Ser Asn Thr Asn Phe Gly Leu Val Ile Arg Asp Thr
        195                 200                 205

Cys Tyr Tyr Arg Ile Gly Arg Tyr Lys Leu Met Arg Thr Phe Thr Asp
    210                 215                 220

Leu Gly His Gly Ala Ser Tyr Ser Ile Glu Glu Asp Glu Thr Ser Asp
225                 230                 235                 240

Tyr Ser Glu Ile His Glu Arg Lys Ile Ser Ser Phe Gln Leu Ile Tyr
                245                 250                 255

Lys Tyr Pro Ser Met Ile Ile Ile Ser Ile Leu Gly Phe Met Leu Thr
            260                 265                 270
```

```
Ile Ala Ile Trp Gly Leu Asn Val Tyr Leu Lys Asn Leu Lys Phe His
            275                 280                 285

Ser Pro Phe Thr Leu Val Ile Ser Phe Ile Val Gly His Cys Leu Ala
        290                 295                 300

Phe Leu Val Glu Pro Phe Asn Tyr Lys Ile Lys Cys Ile Ser Arg Ile
305                 310                 315                 320

Ile Leu Ile Ile Cys Leu Leu Glu Leu Ile Ala Ser Leu Ile Ser
                325                 330                 335

Val Leu Gly Leu Asn Phe Gly Ser Pro Leu Ile Leu Thr Thr Thr Thr
                340                 345                 350

Thr Ile Ser Leu Val Ser Leu Leu Tyr Ile Arg Lys Gln Thr Gln Gly
            355                 360                 365

Val Asn Arg Leu Ala Ala Thr Tyr Ile Ser Arg Ala Leu Ile Ile Gly
370                 375                 380

Leu Tyr Met Thr Val Gly Ile Cys Tyr Ile Phe Ile Lys Thr Ile Asn
385                 390                 395                 400

<210> SEQ ID NO 6
<211> LENGTH: 459
<212> TYPE: PRT
<213> ORGANISM: Canine herpesvirus

<400> SEQUENCE: 6

Met Ser Phe Lys Asn Phe Tyr Leu Ile Tyr Val Ile Ile Ile Phe Ile
1               5                   10                  15

Asn Ser Ile Ile Thr Ser Ala Ser Thr Ser Lys Pro Ser Thr Pro Thr
                20                  25                  30

Ile Ile Pro Thr Ser Ala Asn Glu Ser Pro Ala Ser Ile Asp Thr Thr
            35                  40                  45

Ile Thr Lys Pro Ile Ser Thr Glu Ala Asn Asn Leu Lys Ser Val Ser
        50                  55                  60

Thr Ser Ile Lys Pro Pro Lys Asn Leu Lys Lys Leu Leu Lys Ser
65                  70                  75                  80

Lys Cys Arg Asp Asn Val Ile Tyr Arg Pro Tyr Phe Ser Gln Leu Glu
                85                  90                  95

Ile Asn Cys Thr Ile Thr Lys Lys Gln Asn Leu Ser Asn Pro Leu Ile
            100                 105                 110

Glu Leu Trp Phe Lys Glu Leu Ser Thr Tyr Asn Lys Thr Asn Glu Asn
        115                 120                 125

Val Glu Ser Leu Lys Thr Asp Ile Ser Lys Asn Ile Leu Leu Phe Ser
130                 135                 140

Thr Lys Asn Asn Ser Asp Asn Phe Tyr Asn Asp Phe Leu Leu Gly Ile
145                 150                 155                 160

Gln Asn Gln Pro Val Asn Tyr Lys Leu Tyr Gly Ser Gln Phe Tyr Asp
                165                 170                 175

Asn Gly Asn Ile Leu Leu Asn Ile Lys Ser Val Asp Phe Lys Thr Ser
            180                 185                 190

Gly Ile Tyr Thr Trp Lys Leu Tyr Asn Ser Asn Glu Ser Ile Phe
        195                 200                 205

Glu Thr Phe Lys Ile Gln Val Tyr Ala Tyr His Ser Pro Asn Val Asn
210                 215                 220

Leu Lys Ser Asn Pro Ser Leu Tyr Asn Glu Tyr Ser Ala Ile Cys
225                 230                 235                 240

Thr Ile Ala Asn Tyr Phe Pro Leu Glu Ser Thr Glu Ile Phe Trp Phe
                245                 250                 255
```

```
Asn Asp Gly Gln Pro Ile Asp Lys Lys Tyr Ile Asp Glu Thr Tyr Ser
            260                 265                 270

Val Trp Ile Asp Gly Leu Ile Thr Arg Thr Ser Ile Leu Ser Leu Pro
    275                 280                 285

Phe Ser Glu Ala Met Glu Ser Pro Pro Asn Leu Arg Cys Asn Val Glu
290                 295                 300

Trp Tyr Lys Asn Ser Lys Ala Ser Lys Lys Phe Ser Asn Thr Val Ile
305                 310                 315                 320

Pro Lys Val Tyr Tyr Lys Pro Phe Ile Ser Ile Lys Phe Asp Asn Gly
                325                 330                 335

Leu Ala Ile Cys Asp Ala Lys Cys Val Ser Arg Glu Asn Asn Lys Leu
            340                 345                 350

Gln Trp Leu Val Lys Asp Ile Pro Ile Asn Gly Asp Asp Ile Ile Ser
        355                 360                 365

Gly Pro Cys Leu Asn His Pro Gly Leu Val Asn Ile Gln Asn Lys Ile
    370                 375                 380

Asp Ile Ser Asp Tyr Asp Glu Pro Val Thr Tyr Lys Cys Ser Ile Ile
385                 390                 395                 400

Gly Tyr Pro Ile Ile Phe Pro Asn Phe Tyr Asp Glu Lys Val Phe Asp
                405                 410                 415

Ala Ser Asp Glu Asn Val Ser Lys Ser Met Leu Ile Ser Ile Thr Thr
            420                 425                 430

Ile Ile Gly Gly Ala Ile Phe Val Ile Val Leu Ile Phe Ile Thr Ala
        435                 440                 445

Leu Cys Phe Tyr Cys Ser Lys Asn Asn Lys Ile
    450                 455

<210> SEQ ID NO 7
<211> LENGTH: 115
<212> TYPE: PRT
<213> ORGANISM: Canine herpesvirus

<400> SEQUENCE: 7

Met Ala Gln Leu Val Leu Thr Asp Ile Pro Leu Glu Asp Val Glu Asn
  1               5                  10                  15

Lys Asn Thr Ser Ser Asp Glu Thr Thr Asn Leu Asn Gln Lys Lys
             20                  25                  30

Ser Thr Cys Gln Cys Leu Cys Val Thr Leu Gly Phe Phe Ala Ala Gly
         35                  40                  45

Ile Leu Leu Thr Ile Ala Ala Ile Ile Phe Thr Phe Ile Phe Thr Val
     50                  55                  60

Pro Leu Glu Met Leu Gly Ser Ile Asn Cys Pro Pro Ser Thr Phe Gly
65                  70                  75                  80

Ile Asp Asn Val Cys Ile Glu Pro Ile Lys Lys Ser Ile Asn Ser Tyr
             85                  90                  95

Ser Glu Leu Ser Lys Ile Cys Tyr Asp Arg Leu Ser Asn Pro Ile Asn
            100                 105                 110

Gln Ser Thr
        115

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence:
``` oligonucleotide

<400> SEQUENCE: 8
ctagtccagc aaggtggatc gatatcgggc cca          33

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
ctagtgggcc cgatatcgat ccaccttgct gga          33

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
cagctttatg tttttattgt tc          22

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
aaagaattct acaactgttt aataaagac          29

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
actccagcta catgggatat cgggcccatc gatcag          36

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
ctgatcgatg ggcccgatat cccatgtagc tggagt          36

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence:
      oligonucleotide

```
<400> SEQUENCE: 14
agcgttaacc tcaaaagcca aatttacact tcccg                                          35

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
cccaagcttt tctaaagccc atttataaat aataaatg                                       38

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
aattcccagc tacatgggat atcgggccca tcgatc                                         36

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
caaggatcga tgggcccgat atcccatgta gctggg                                         36

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
ggagatctag taaattaaat agtaattcat ttaatg                                         36

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19
cagtcgcgaa gatgaaaata aaatccatcg aag                                            33

<210> SEQ ID NO 20
<211> LENGTH: 38
<212> TYPE: DNA
<213> ORGANISM: Artificial Sequence
<220> FEATURE:
<223> OTHER INFORMATION: Description of Artificial Sequence:
      oligonucleotide
```

```
<400> SEQUENCE: 20
aattggcagc tacatgggat atcgggccca tcgataat                              38

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
attatcgatg ggcccgatat cggatgtagc tggc                                  34

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
ttgcggccgc atgctcccct accaagacaa gg                                    32

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
ttggtacctt aacggttaca tgagaatc                                         28

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 24
ttgggtaccg cctcgactct aggcggccgc                                       30

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 25
ttgggtaccg gatccgaaaa aacctcccac ac                                    32

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 26
```

```
ttgcggccgc atgcacaggg gaatccccaa aagc                                34

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27
ttggtacctc agagtgatct cacatagg                                       28

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28
ctagtccagc aaggtgtcga cggatcgata tcgggccca                           39

<210> SEQ ID NO 29
<211> LENGTH: 39
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
ctagtgggcc cgatatcgat ccgtcgacac cttgctgga                           39

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30
ttgcggccgc atggttcctc aggctctcct g                                   31

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 31
ttggtacctc acagtctggt ctcaccccca c                                   31
```